United States Patent
Bailey et al.

(10) Patent No.: US 9,187,778 B2
(45) Date of Patent: Nov. 17, 2015

(54) EFFICIENT LIGHT HARVESTING

(75) Inventors: Shaun Bailey, Los Altos, CA (US);
Yuen Yee Tam, San Leandro, CA (US);
Bertrand Vick, Emeryville, CA (US)

(73) Assignee: Aurora Algae, Inc., Hayward, CA (US)

( * ) Notice: Subject to any disclaimer, the term of this patent is extended or adjusted under 35 U.S.C. 154(b) by 943 days.

(21) Appl. No.: 12/704,035

(22) Filed: Feb. 11, 2010

(65) Prior Publication Data

US 2011/0197306 A1  Aug. 11, 2011

Related U.S. Application Data

(60) Provisional application No. 61/175,444, filed on May 4, 2009.

(51) Int. Cl.
*C12Q 1/02* (2006.01)
*A01H 1/06* (2006.01)

(52) U.S. Cl.
CPC .. *C12Q 1/02* (2013.01); *A01H 1/06* (2013.01); *G01N 2333/405* (2013.01)

(58) Field of Classification Search
None
See application file for complete search history.

(56) References Cited

U.S. PATENT DOCUMENTS

| | | |
|---|---|---|
| 1,926,780 A | 9/1933 | Lippincott |
| 3,220,706 A | 11/1965 | Valdespino |
| 3,468,057 A | 9/1969 | Buisson |
| 3,897,000 A | 7/1975 | Mandt |
| 3,955,318 A | 5/1976 | Hulls |
| 4,003,337 A | 1/1977 | Moore |
| 4,115,949 A | 9/1978 | Avron et al. |
| 4,217,728 A | 8/1980 | Shimamatsu et al. |
| 4,267,038 A | 5/1981 | Thompson |
| 4,365,938 A | 12/1982 | Warinner |
| 4,535,060 A | 8/1985 | Comai |
| 4,658,757 A | 4/1987 | Cook |
| 4,813,611 A | 3/1989 | Fontana |
| 5,105,085 A | 4/1992 | McGuire et al. |
| 5,130,242 A | 7/1992 | Barclay |
| 5,227,360 A | 7/1993 | Sherba et al. |
| 5,338,673 A | 8/1994 | Thepenier et al. |
| 5,353,745 A | 10/1994 | Fahs, II |
| 5,478,208 A | 12/1995 | Kasai |
| 5,518,990 A | 5/1996 | Ushio et al. |
| 5,527,456 A | 6/1996 | Jensen |
| 5,539,133 A | 7/1996 | Kohn et al. |
| 5,564,630 A | 10/1996 | Giles et al. |
| 5,573,669 A | 11/1996 | Jensen |
| 5,658,076 A | 8/1997 | Crump et al. |
| 5,658,767 A | 8/1997 | Kyle |
| 5,823,781 A | 10/1998 | Hitchcock et al. |
| 5,871,952 A | 2/1999 | Ghirardi et al. |
| 6,000,551 A | 12/1999 | Kanel et al. |
| 6,117,313 A | 9/2000 | Goldman |
| 6,166,231 A | 12/2000 | Hoeksema |
| 6,192,833 B1 | 2/2001 | Brune et al. |
| 6,372,460 B1 | 4/2002 | Gladue et al. |
| 6,447,681 B1 | 9/2002 | Carlberg et al. |
| 6,524,486 B2 | 2/2003 | Borodyanski et al. |
| 6,579,714 B1 | 6/2003 | Hirabayashi et al. |
| 6,626,738 B1 | 9/2003 | Shank |
| 6,736,572 B2 | 5/2004 | Geraghty |
| 6,750,048 B2 | 6/2004 | Ruecker et al. |
| 6,831,040 B1 | 12/2004 | Unkefer et al. |
| 6,871,195 B2 | 3/2005 | Ryan et al. |
| 6,896,804 B2 | 5/2005 | Haerther et al. |
| 6,936,459 B1 | 8/2005 | Venkatesh et al. |
| 6,944,013 B2 | 9/2005 | Yang |
| 7,333,195 B2 | 2/2008 | Krei.beta. et al. |
| 7,381,326 B2 | 6/2008 | Haddas |
| 7,391,608 B2 | 6/2008 | Tsai |
| 7,669,780 B2 | 3/2010 | Sugano et al. |
| 7,682,821 B2 | 3/2010 | Woods et al. |
| 7,748,650 B1 | 7/2010 | Sloan |
| 7,770,322 B2 | 8/2010 | Huntley et al. |
| 8,143,051 B2 | 3/2012 | Weissman et al. |
| 8,507,254 B1 | 8/2013 | Abuhasel |
| 8,748,160 B2 | 6/2014 | Parsheh et al. |
| 8,752,329 B2 | 6/2014 | Parsheh et al. |
| 8,769,867 B2 | 7/2014 | Parsheh et al. |

(Continued)

FOREIGN PATENT DOCUMENTS

| | | |
|---|---|---|
| AU | 2010210982 | 9/2014 |
| CN | 102164492 A1 | 8/2011 |

(Continued)

OTHER PUBLICATIONS

Mitra, M. and Melis, A. Optics Express, Dec. 22, 2008; vol. 16, No. 26, 14 pages.*
Rodolphi, L. et al. Biotechnology and Bioengineering (2008); vol. 102, No. 1, Jan. 1, 2009; pp. 100-112.*
Santin-Montanaya, I. Optimal growth of *Dunaliella primolecta* in axenic conditions to assay herbicides, Chemosphere, 66, Elsevier 2006, pp. 1315-1322.
Felix, R. Use of the cell wall-less alga *Dunaliella bioculata* in herbicide screening tests, Annals of Applied Biology, 113, 1988, pp. 55-60.
Janssen, M. Photosynthetic efficiency of *Dunaliella tertiolecta* under short light/dark cycles, Enzyme and Microbial Technology, 29, 2001, pp. 298-305.

(Continued)

*Primary Examiner* — Russell Kallis
(74) *Attorney, Agent, or Firm* — Carr & Ferrell LLP

(57) ABSTRACT

Various aspects provide for genetically modifying photosynthetic cells. In some cases, an integrated light harvesting efficiency of photosynthetic cells may be increased by reducing the amount of incident light that is absorbed but not used for photosynthesis. In some cases, an increased transparency may be associated with an increased light harvesting efficiency when absorption due to non-photosynthetic processes is reduced. A reduced capacity of various light-harvesting antenna apparatus may increase transparency. In some cases, a capacity of an organism to adapt to varying light levels may be reduced, and in certain cases, a modified organism may have a reduced ability to acclimate to a low light irradiance.

13 Claims, 18 Drawing Sheets

(56) References Cited

U.S. PATENT DOCUMENTS

| | | |
|---|---|---|
| 8,940,340 B2 | 1/2015 | Weissman et al. |
| 2002/0105855 A1 | 8/2002 | Behnke et al. |
| 2003/0038566 A1 | 2/2003 | Qiu |
| 2003/0116502 A1 | 6/2003 | DeBusk et al. |
| 2003/0140021 A1 | 7/2003 | Ryan et al. |
| 2003/0199490 A1 | 10/2003 | Antoni-Zimmermann et al. |
| 2004/0121447 A1 | 6/2004 | Fournier |
| 2004/0161364 A1 | 8/2004 | Carlson |
| 2004/0262219 A1 | 12/2004 | Jensen |
| 2005/0064577 A1 | 3/2005 | Berzin |
| 2005/0095569 A1 | 5/2005 | Franklin |
| 2005/0164192 A1 | 7/2005 | Graham et al. |
| 2005/0170479 A1 | 8/2005 | Weaver et al. |
| 2005/0181345 A1 | 8/2005 | Bradbury et al. |
| 2005/0260553 A1 | 11/2005 | Berzin |
| 2005/0273885 A1 | 12/2005 | Singh et al. |
| 2006/0031087 A1 | 2/2006 | Fox et al. |
| 2006/0044259 A1 | 3/2006 | Hotelling et al. |
| 2006/0045750 A1 | 3/2006 | Stiles |
| 2006/0122410 A1 | 6/2006 | Fichtali et al. |
| 2006/0155558 A1 | 7/2006 | Corpening |
| 2006/0166243 A1 | 7/2006 | Su et al. |
| 2006/0192690 A1 | 8/2006 | Philipp |
| 2007/0115626 A1 | 5/2007 | Peng et al. |
| 2007/0155006 A1 | 7/2007 | Levin |
| 2007/0289206 A1 | 12/2007 | Kertz |
| 2008/0118964 A1 | 5/2008 | Huntley et al. |
| 2008/0120749 A1 | 5/2008 | Melis et al. |
| 2008/0155888 A1 | 7/2008 | Vick et al. |
| 2008/0155890 A1 | 7/2008 | Oyler |
| 2008/0160488 A1 | 7/2008 | Younkes et al. |
| 2008/0160591 A1 | 7/2008 | Willson et al. |
| 2008/0160593 A1 | 7/2008 | Oyler |
| 2008/0220486 A1 | 9/2008 | Weiss |
| 2008/0293132 A1 | 11/2008 | Goldman et al. |
| 2009/0011492 A1 | 1/2009 | Berzin |
| 2009/0029445 A1 | 1/2009 | Eckelberry et al. |
| 2009/0061928 A1 | 3/2009 | Lee et al. |
| 2009/0126265 A1 | 5/2009 | Rasmussen et al. |
| 2009/0137031 A1 | 5/2009 | Hirabayashi |
| 2009/0148931 A1 | 6/2009 | Wilkerson et al. |
| 2009/0151241 A1 | 6/2009 | Dressler et al. |
| 2009/0162919 A1 | 6/2009 | Radaelli et al. |
| 2009/0186860 A1 | 7/2009 | Huff et al. |
| 2009/0234146 A1 | 9/2009 | Cooney et al. |
| 2009/0319338 A1 | 12/2009 | Parks et al. |
| 2009/0325270 A1 | 12/2009 | Vick et al. |
| 2010/0022393 A1 | 1/2010 | Vick |
| 2010/0068772 A1 | 3/2010 | Downey |
| 2010/0100520 A1 | 4/2010 | Dargue et al. |
| 2010/0170149 A1 | 7/2010 | Keeler et al. |
| 2010/0170150 A1 | 7/2010 | Walsh, Jr. |
| 2010/0183744 A1 | 7/2010 | Weissman et al. |
| 2010/0196995 A1 | 8/2010 | Weissman et al. |
| 2010/0198659 A1 | 8/2010 | Meltzer et al. |
| 2010/0210003 A1 | 8/2010 | King |
| 2010/0257781 A1 | 10/2010 | Batty et al. |
| 2010/0260618 A1 | 10/2010 | Parsheh et al. |
| 2010/0261922 A1 | 10/2010 | Fleischer et al. |
| 2010/0314324 A1 | 12/2010 | Rice et al. |
| 2010/0323387 A1 | 12/2010 | Bailey et al. |
| 2010/0325948 A1 | 12/2010 | Parsheh et al. |
| 2010/0327077 A1 | 12/2010 | Parsheh et al. |
| 2011/0016773 A1 | 1/2011 | Nichols et al. |
| 2011/0023360 A1 | 2/2011 | Ryan et al. |
| 2011/0051354 A1 | 3/2011 | Fan et al. |
| 2011/0136212 A1 | 6/2011 | Parsheh et al. |
| 2011/0197306 A1 | 8/2011 | Bailey et al. |
| 2011/0258915 A1 | 10/2011 | Subhadra |
| 2011/0287531 A1 | 11/2011 | Hazlebeck |
| 2011/0287544 A1 | 11/2011 | Berzin et al. |
| 2012/0252104 A1 | 10/2012 | Waibel et al. |
| 2012/0272574 A1 | 11/2012 | Parsheh et al. |
| 2013/0130909 A1 | 5/2013 | Vick et al. |

FOREIGN PATENT DOCUMENTS

| | | |
|---|---|---|
| CN | 102348793 A1 | 2/2012 |
| CN | 102459585 A1 | 5/2012 |
| CN | 102575221 A1 | 7/2012 |
| CN | 103649551 A | 3/2014 |
| CN | 103687938 A | 3/2014 |
| EP | 2427551 A1 | 3/2012 |
| HK | 1168381 A1 | 12/2012 |
| IL | 21449 | 1/2015 |
| IN | Journal 52/2012 A1 | 12/2012 |
| IN | Journal 12/2013 A1 | 3/2013 |
| IN | Journal 20/2013 A1 | 5/2013 |
| IN | Journal 37/2013 A1 | 9/2013 |
| JP | 09173050 A | 7/1997 |
| MX | 20110000934 A1 | 7/2011 |
| MX | 2011008222 A1 | 1/2012 |
| MX | 322192 | 7/2014 |
| WO | 2004106238 A2 | 12/2004 |
| WO | 2009037683 A1 | 3/2009 |
| WO | 2009149519 A1 | 12/2009 |
| WO | 2010008490 A1 | 1/2010 |
| WO | 2010011335 A1 | 1/2010 |
| WO | 2010090760 A1 | 8/2010 |
| WO | 2010129041 A1 | 11/2010 |
| WO | 2010147648 A1 | 12/2010 |
| WO | 2011002487 A1 | 1/2011 |
| WO | 2012149214 A1 | 11/2012 |
| WO | 2012170737 A1 | 12/2012 |

OTHER PUBLICATIONS

Saenz, M.E. Effects of Technical Grade and a Commercial Formulation of Glyphosate on Algal Population Growth, Bulletin of Environmental Contamination Toxicology, 1997, pp. 638-644.
Christy et al., "Effects of Glyphosate on Growth of *Chlorella*," Weed Science, vol. 29, Issue 1, Jan. 1981, pp. 5-7.
Roessler et al., "Genetic Engineering Approaches for Enhanced Production of Biodiesel Fuel from Microalgae," ACS Symposium Series; American Chemical Society, 1994, pp. 255-270.
Grima et al. "Recovery of Microalgal Biomass in Metabolites: Process Options and Economics," Biotechnology Advances 20, 2003, pp. 491-515.
Knuckey et al. "Production of Microalgal Concentrates by Flocculation and their Assessment as Aquaculture Feeds," Aquacultural Engineering 35, 2006, pp. 300-313.
Applying [online] retrieved from: http://www.merriam-webster.com/dictionary/applying, on May 21, 2011; 3 pages.
Cohen, "Chemicals from MicroAlgae", 1999, CRC Press, pp. 49 and 51.
Kureshy et al., "Effect of Ozone Treatment on Cultures of *Nannochloropsis oculata, Isochrysis galbana*, and *Chaetoceros gracilis*," Journal of the World Aquaculture Society, 1999, 30(4), pp. 473-480.
Liao et al. "An Overview of Live Feeds Production System Design in Taiwan," Rotifer and Microalgae Culture Systems, Proceedings of a US-Asia Workshop, Honolulu, HI, 1991, pp. 135-150.
Kanematsu et al., "Methods to Repress the Growth of a Nannochloropsis-Grazing Microflagellate," Nippon Suisan Gakkaishi 55, 1989, pp. 1349-1352 (English Translation).
Csogor et al., "Light Distribution in a Novel Photobioreactor—Modelling for Optimization," Journal of Applied Phycology, vol. 13, 2001, pp. 325-333.
Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.
Zittelli et al., "Mass Cultivation of *Nannochloropsis* Sp. in Annular Reactors," Journal of Applied Phycology, vol. 15, pp. 107-113, Mar. 2003.
Strzepek et al., "Photosynthetic Architecture Differs in Coastal and Oceanic Diatoms," Nature, vol. 431, pp. 689-692, Oct. 2004.
Lee et al., "Isolation and Characterization of a Xanthophyll Aberrant Mutant of the Green Alga *Nannochloropsis oculata*," Marine Biotechnology, 2006, vol. 8, pp. 238-245.
NCBI entry EE109892 (Jul. 2006) [Retrieved from the Internet on Oct. 19, 2009, <http://www.ncbi.nlm.nih.gov/nucest/

(56) References Cited

OTHER PUBLICATIONS

EE109892?ordinalops=1&itool=EntrezSystem2.Pentrez.Sequence. Sequence_ResultsPanel. Sequence_RVDocSum>].
Berberoglu et al., "Radiation Characteristics of *Chlamydomonas reinhardtii* CC125 and its truncated chlorophyll antenna transformants tla1, tlaX, and tla1-CW+," International Journal of Hydrogen Energy, 2008, vol. 33, pp. 6467-6483.
Ghirardi et al., "Photochemical Apparatus Organization in the Thylakoid Membrane of *Hordeum vulgare* wild type and chlorophyll b-less chlorina f2 mutant," Biochimica et Biophysica Act (BBA)—Bioengergetics, vol. 851, Issue 3, Oct. 1986, pp. 331-339 (abstract only).
Steinitz et al., "A mutant of the cyanobacterium *Plectonema boryanum* resistant to photooxidation," Plant Science Letters, vol. 16, Issues 2-3, 1979, pp. 327-335 (abstract only).
Koller et al., "Light Intensity During Leaf Growth Affects Chlorophyll Concentration and CO2 Assimilation of a Soybean Chlorophyll Mutant," Crop Science, 1974, vol. 14, pp. 779-782 (abstract only).
Shikanai et al., "Identification and Characterization of Arabidopsis Mutants with Reduced Quenching of Chlorophyll Fluorescence," Plant and Cell Physiology, 1999, vol. 40, No. 11, pp. 1134-1142 (abstract only).
Andersen, "Algal Culturing Techniques," 2005, p. 208.
Ben-Amotz, Ami. "Large-Scale Open Algae Ponds," presented at the NREL-AFOSR Joint Workshop on Algal Oil for Get Fuel Production in Feb. 2008.
Ebeling et al., "Design and Operation of a Zero-Exchange Mixed-Cell Raceway Production System," 2nd Int'l Sustainable Marine Fish Culture Conference and Workshop, Oct. 2005.
Ebeling et al., "Mixed-Cell Raceway: Engineering Design Criteria, Construction, and Hydraulic Characterization," North American Journal of Aquaculture, 2005, 67: 193-201 (abstract only).
Labatut et al., "Hydrodynamics of a Large-Scale Mixed-Cell Raceway (MCR): Experimental Studies," Aquacultural Engineering vol. 37, Issue 2, Sep. 2007, pp. 132-143.
Kizilisoley et al., "Micro-Algae Growth Technology Systems," Presented by Selim Helacioglu, Soley Institute, 2008.
Kent BioEnergy, "Fish Farm Empties Its Ponds to Grow Algae for Biofuels," Apr. 17, 2009 (http://www-csgc.ucsd.edu/newsroom/newsreleases/2009/algaeforbiofuls.html).
Hoyt et al., "Waves on Water Jets," J. Fluid Mech., 1977, vol. 83, Part 1, pp. 119-127.
Dodd, "Elements of Pond Design and Construction," CRC Handbook of Microalgal Mass Culture, Richmond, ed., Boca Raton, FL.: CRC Press, 1986, pp. 265-283, see entire document, especially Fig. 1; p. 268, para. 3 to p. 269, para. 1; p. 270, para. 1.
International Search Report mailed Sep. 16, 2009 for Application No. PCT/US2009/004296, filed Jul. 24, 2009.
Written Opinion of the International Searching Authority mailed Sep. 16, 2009 for Application No. PCT/US2009/004296, filed Jul. 24, 2009.
Office Action mailed Nov. 14, 2012 in China Patent Application No. 200980138072.X, filed Jul. 24, 2009.
Official Action mailed Jul. 10, 2012 in Mexico Patent Application No. MX/a/2011/000934, filed Jul. 24, 2009.
Official Action mailed Mar. 5, 2013 in Mexico Patent Application No. MX/a/2011/000934, filed Jul. 24, 2009.
Duarte et al., "Glyphosate (GP) Effects with Emphasis on Aquatic Organisms," Colunbia Orinoquia, ISSN: 0121-3709, pp. 70-100, 2004.
Technical Card: Glyphosate, Document filed for the Pesticide Action Network and the Alternatives Thereof, for Latin America (RAP-AL)—Communications and Administration Office, Apr. 2008.
Republic of Columbia Department of Environment, Housing and Territorial Development, Resolution (1009), published Jun. 17, 2008. (36 pages).
International Search Report and Written Opinion of the International Searching Authority mailed May 3, 2010 for Application No. PCT/US2010/000346, filed Feb. 4, 2010.
Patent Examination Report No. 1 mailed Jan. 9, 2013 in Australia Patent Application 2010210982, filed Feb. 4, 2010.
First Office Action mailed Nov. 5, 2012 in China Patent Application No. 201080012755.3, filed Feb. 4, 2010.
Official Action mailed Sep. 17, 2012 in Mexico Patent Application No. MX/a/2011/008222, filed Feb. 4, 2010.
International Search Report and Written Opinion of the International Searching Authority mailed Aug. 30, 2010 for Application No. PCT/US2010/001731, filed Jun. 15, 2010.
Notice on the First Office Action mailed Dec. 14, 2012 in Chinese Application No. 201080036170.5 filed Jun. 15, 2010.
International Search Report and Written Opinion of the International Searching Authority mailed Aug. 19, 2010 for Application No. PCT/US2010/001755, filed Jun. 16, 2010.
International Search Report and Written Opinion of the International Searching Authority mailed Jul. 31, 2012 for Application No. PCT/US2012/035290, filed Apr. 26, 2012.
International Search Report and Written Opinion of the International Searching Authority mailed Jul. 30, 2010 for Application No. PCT/US2010/001315, filed May 4, 2010.
First Office Action mailed Oct. 25, 2012 in China Patent Application No. 201080027531.X, filed May 4, 2010.
Extended European Search Report mailed Oct. 5, 2012 in European Patent Application 10772376.9, filed on May 4, 2010.
Polle et al., "tla1, a DNA insertional transformant of the green alga *Chlamydomonas reinhardtii* with a truncated light-harvesting chlorophyll antenna size," Planta, vol. 217, No. 1, May 2003, pp. 49-59.
Lawrence et al., "Variation in Plants Regenerated from Vacuolate and Evacuolate Protoplasts," Plant Science, vol. 50, No. 2, 1987, pp. 125-132.
Beckmann et al., "Improvement of light to biomass conversion by de-regulation of light-harvesting protein translation in *Chlamydomonas reinhardtii*," Journal of Biotechnology, vol. 142, No. 1, 2009, pp. 70-77.
International Search Report and Written Opinion of the International Searching Authority mailed Aug. 16, 2012 for Application No. PCT/US2012/041425, filed Jun. 7, 2012.
European Search Report mailed Oct. 5, 2012 in European Patent Application No. 10772376.9, filed May 4, 2010.
Examination Report mailed Feb. 20, 2013 in Australian Application No. 2009274500 filed Jul. 24, 2009.
Notice on the Second Office Action mailed Jun. 20, 2013 in Chinese Application No. 201080012755.3 filed Feb. 4, 2010.
Notice on the Second Office Action mailed Jul. 5, 2013 in Chinese Application No. 201080027531.X filed May 4, 2010.
Examination Report mailed Aug. 22, 2013 in Australian Application No. 2010260530 filed Jun. 15, 2010.
First Office Action mailed Aug. 29, 2013 in Mexican Application No. MX/a/2011/013710 filed Jun. 15, 2010.
Examination Report mailed Aug. 29, 2013 in European Application No. 10772376.9 filed May 4, 2010.
Examination Report mailed Sep. 19, 2013 in Australian Application No. 2010245255 filed May 4, 2010.
Notice on the Second Office Action mailed Sep. 24, 2013 in Chinese Application No. 200980138072.X filed Jul. 24, 2009.
Exposure on the Growth and Physiology of *Nostoc sphaeroides*, an Edible Cyanobacterium of Paddy Rice Fields, Acta Hydrobiologica Sinica, Jul. 2008 vol. 32, No. 4, pp. 462-468.
HCAPLUS abstract 1997; 248650 (1997).
HCAPLUS abstract 2005; 600349 (2005).
HCAPLUS abstract 2007; 1143765 (2007).
Notice on the Second Office Action mailed Oct. 24, 2013 in Chinese Application No. 201080036170.5 filed Jun. 15, 2010.
Tucker (Water Treatment, 1998, Springer, pp. 1-754).
Vinneras et al (The potential for disinfection of separated faecal matter by urea and by peracetic acid for hygienic nutrient recycling, 2003, Bioresources Technology, vol. 89, pp. 155-161).
CCAP website, f2 media recipe, 2005.
Palanichamy et al (Observations on the long term preservation and culture of the marine microalga, *Nannochloropsis oculata*, 2004, Journal of Marine Biology Association of India, vol. 46, pp. 98-103).
Office Action mailed Nov. 11, 2013 in Mexican Application No. MX/a/2011/000934 filed Jul. 24, 2009.

(56) References Cited

OTHER PUBLICATIONS

Office Action mailed Jan. 30, 2014 in Mexican Application No. MX/a/2011/013710 filed Jun. 15, 2010.
Notice of Allowance mailed Mar. 7, 2014 in Australian Application No. 2010210982 filed Feb. 4, 2010.
Office Action mailed Feb. 12, 2014 in Chinese Application No. 201080012755.3 filed Feb. 4, 2010.
Office Action mailed Mar. 4, 2014 in Chinese Application No. 201080027531.X filed May 4, 2010.
Office Action mailed Mar. 27, 2014 in Israeli Application No. 210805 filed Jul. 24, 2009.
Notice of Allowance mailed Jun. 16, 2014 in Mexican Application No. MX/a/2011/013710 filed Jun. 15, 2010.
Office Action mailed Jun. 12, 2014 in Chinese Application No. 200980138072.X filed Mar. 24, 2011.
Office Action mailed Jun. 20, 2014 in Chinese Application No. 201080036170.5 filed Jun. 15, 2010.
Office Action mailed Jun. 9, 2014 in Israeli Application No. 216989 filed Dec. 15, 2011.
Gonen-Zurgil, Y., Carmeli-Schwartz, Y., Sukenik, A. (1996). Selective effect of the herbicide DCMU on unicellular algae—a potential tool to maintain monoalgal mass culture of *Nannochloropsis*. Journal of Applied Phycology, 8: 415-419. (Full Article).
Podola, B., Melkonian, M. (2005). Selective real-time herbicide monitoring by an array chip biosensor employing diverse microalgae. Journal of Applied Phycology, 17: 261-271. (Full Article).
Fayez, K., Abd-Elfattah, Z. (2007). Alteration in Growth and Physiological Activities in *Chlorella vulgaris* under the Effect of Photosynthetic Inhibitor Diuron. International Journal of Agriculture, 9: 631-634. (Full Article).

Fawley et al. "Observations on the Diversity and Ecology of Freshwater *Nannochloropsis* (Eustigmatophyceae), with Descriptions of New Taxa" Protist. vol. 158, Issue 3. Jul. 18, 2007, pp. 325-336.
Pathak et al. "The use of chemicals in aquaculture in India." (2000) Web. <http://hdl.handle.net/10862/604>.
"Ocean Water: Salinity." Office of Naval Research. Web. <http://www.onr.navy.mil/focus/ocean/water/salinity1.htm>.
Office Action mailed Jul. 14, 2014 in Mexican Application No. MX/a/2011/000934 filed Jul. 24, 2009.
Office Action mailed Sep. 7, 2014 in Israeli Application No. 216110 filed May 4, 2010.
Office Action mailed Sep. 11, 2014 in Israeli Application No. 210805 filed Jul. 24, 2009.
Lembi et al. (2009). Identifying and Managing Aquatic Vegetation. Aquatic Plant Management. https://www.extension.purdue.edu/extmedia/APM/APM_3_W.pdf.
Notice of Allowance mailed Nov. 3, 2014 in Australian Application No. 2009274500 filed Jul. 24, 2009.
Office Action mailed Oct. 20, 2014 in European Application No. 10772376.9 filed Nov. 9, 2011.
Office Action mailed Nov. 15, 2014 in Chinese Application No. 201080027531.X filed Dec. 20, 2011.
Office Action mailed Sep. 17, 2014 in Mexican Application No. MX/a/2011/011702 filed May 4, 2010.
Office Action mailed Jul. 6, 2015 in Mexican Application No. MX/a/2013/014301 filed Jun. 7, 2012.
Office Action mailed Jun. 30, 2015 in Chinese Application No. 201280031871.9 filed Apr. 26, 2012.

* cited by examiner

EFFICIENT LIGHT HARVESTING

CROSS REFERENCE TO RELATED APPLICATIONS

This application claims the priority benefit of U.S. provisional patent application No. 61/175,444, filed May 4, 2009.

BACKGROUND

1. Technical Field

The present invention relates to improving the efficiency with which photosynthetic organisms use light.

2. Description of Related Art

Photosynthetic organisms use energy from light to form chemical bonds. Energy embodied within the chemical bonds may be used at a later date. As such, chemical bonds provide a storage mechanism for the energy associated with incident light.

A supply of light is often finite in a given period of time. For a given fluence of incident light, photosynthetic organisms may use some of the light to perform photosynthesis. Some of the light may not be used for photosynthesis. Some light may be converted to heat. Some light may be absorbed and reemitted (e.g., fluoresced). Some light may damage the organism. Light that is not used for photosynthesis may not be converted into stored chemical energy within the organism, and so the energy associated with this unconverted light may not be available for subsequent use. Improving the conversion of incident light to biomass (e.g., increasing the percentage of incident energy converted to chemical bonds) may increase the efficiency of biomass production, which may increase the amount of incident solar energy available for subsequent use.

SUMMARY OF THE INVENTION

Various aspects provide for selecting a natural and/or wild type photosynthetic organism. Cells of the wild type organism may have a first transparency associated with light transmission through the cells. The organism may be subject to mutagenesis to create one or more mutated photosynthetic organisms. Transparencies of the cells of the mutated organisms may be determined, and a mutated organism having a transparency greater than that of the wild type organism may be selected.

In some cases, growth rates may be measured. A mutated organism and/or a plurality of mutated organisms (e.g., a suspension of organisms) may have a higher growth rate than a similar wild type. In some cases, more transparent organisms or cells may have a higher overall growth rate. Growth rate may be measured in terms of total biomass (e.g., dry matter) and/or quantities of certain components or chemicals (carbohydrates, proteins, lipids, nucleic acids, and the like). Growth rate may include or be normalized to a quantity of incident radiation (e.g., light or sunlight).

Organisms may include crops such as corn, rice, wheat, sugarcane, and the like. Organisms may include trees, such as poplar, conifers, jatropha, palm, and the like. Organisms may include grasses such as prairie grasses, switchgrass, *Miscanthus*, and the like. Organisms may include single cell organisms such as algae, diatoms, cyanobacteria, and the like.

In some cases, mutated organisms may be identified optically, for example using fluorescence. In certain cases, a more transparent organism may have a paler green color than a less transparent version. Organisms may be identified using various responses, such as a photosystem I response, photosystem II response, nonphotochemical quenching, photosynthetic rate, irradiance threshold, and the like.

In some embodiments, an organism may be modified to reduce a sensitivity of one or more light harvesting apparatus and/or mechanisms. In some cases, a light harvesting antenna (e.g., associated with photosystem II) may be modified to have a reduced effectiveness or efficiency as compared to an unmodified (e.g., wild type) organism. In some cases, modification of an organism may result in a modified organism having a reduced ability to adapt to changing light conditions. In certain examples, this reduced ability may be manifest as a reduced ability to adapt to low light conditions. Certain cells and/or organisms may be described as being "locked" into an acclimation state associated with high irradiance levels, despite exposure to low irradiance levels.

Organisms may be mutated (e.g., using mutagenesis) to create one or more mutated versions of the organism. Mutated versions may be screened for one or more properties. In some cases, a plurality of mutated organisms (e.g., a suspension of algae or diatoms) may have an increased transparency and a higher growth rate than an otherwise equivalent plurality of wild type organisms.

DETAILED DESCRIPTION OF THE INVENTION

Figure 1:
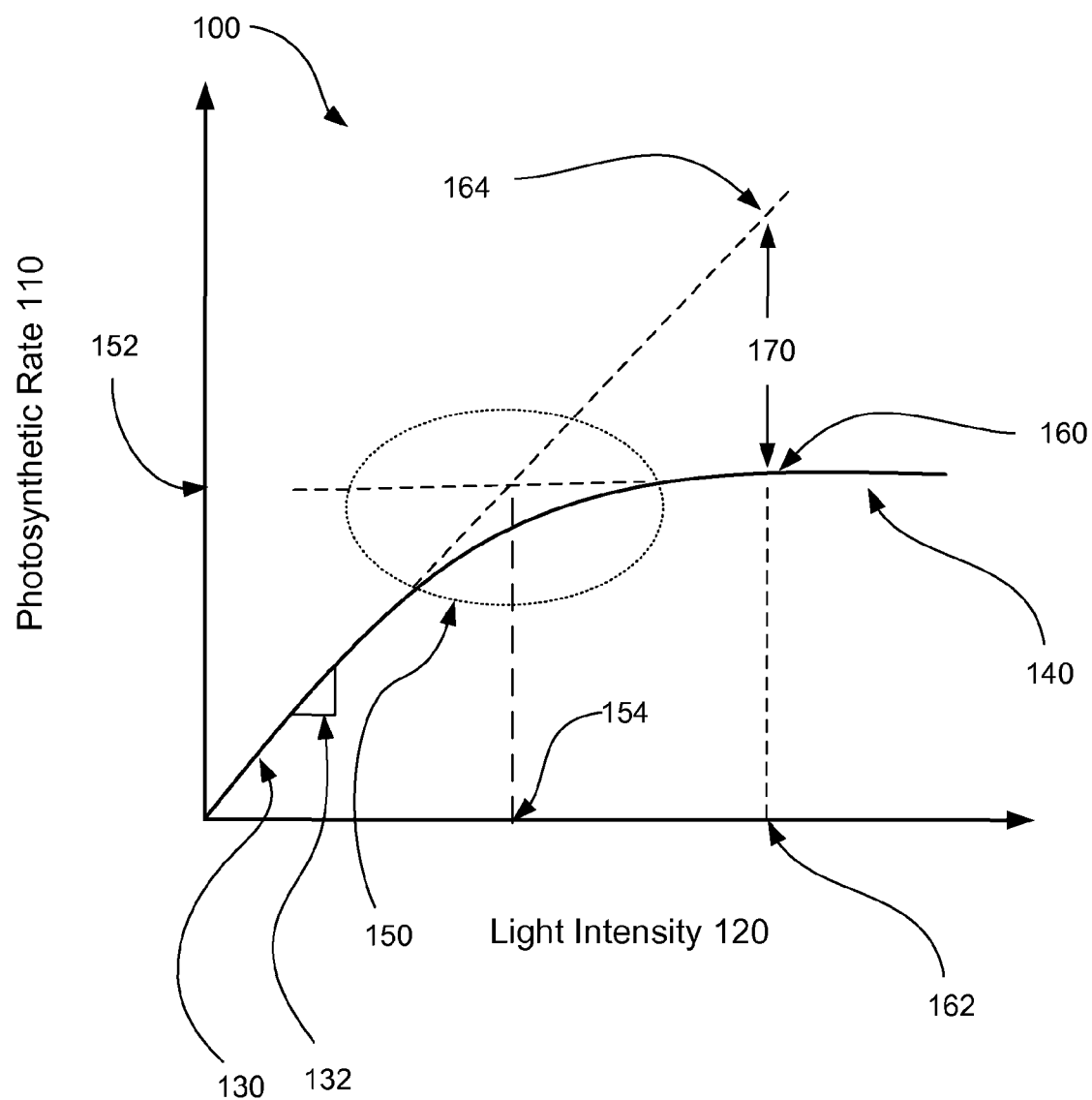
FIG. 1 illustrates an exemplary saturation response of a photosynthetic cell, according to some embodiments.

Many organisms include cells, organelles, membranes, and the like that perform photosynthesis. A photosynthetic cell may be modified to change (e.g., increase or decrease) its transparency to light. Modification of a cell may include mutating the cell, and may include performing PCR Mutagenesis, Transposon Mutagenesis, Site-directed Mutagenesis, Directed Mutagenesis, Random Mutagenesis, Insertional Mutagenesis, Targeted Mutagenesis, and the like on the cell.

Transparency may be changed by modifying the size of a light harvesting antenna (LHA). In some cases, LHA associated with Photosystem II (PSII) may be modified in a manner that increases transparency. A reduced transparency of a first cell may result in a greater amount of light passing through the first cell to a second cell. The second cell may productively utilize a portion of light that might have been dissipated by the first cell were it not to pass through the first cell.

A plurality of cells having increased transparency may have a higher overall photochemical efficiency than a similar plurality having reduced (e.g., native) transparency. A light harvesting efficiency of a population of photosynthetic cells may be increased by reducing the total amount of incident light absorbed, scattered, converted, or otherwise consumed by non-photosynthetic reactions. In some cases, an overall or integrated growth rate of the group of more transparent cells may be as great as, or even greater than, the growth rate of the group of less transparent cells. In some cases, a more transparent cell may be less susceptible to damage, particularly under bright light conditions. A more transparent cell may be more robust to changing light conditions (e.g., passing from a low light condition to a high light condition).

An efficiency with which light is harvested by a group of photosynthetic cells may increase the amount of incident energy that is converted to chemical bonds. An increase in light harvesting efficiency may be manifest in a reduction in the incident energy needed to create biomass, which may be manifest as a concomitant reduction in the energy needed to produce biomass-derived products, such as biochemicals, biofuels, ethanol, esters, alkanes, nutrients, food, supplements, and/or other products derived from photosynthetic organisms.

Many photosynthetic cells have a finite capacity to utilize incident light for photosynthesis. A low intensity light may be efficiently utilized (e.g., substantially converted to chemical energy, or converted as efficiently as quantum or physiological limits allow). A more intense light may "overpower" the organism's photosynthesis capabilities, resulting in a substantial portion of the incident light not being used for photosynthesis. Such unused light may be absorbed, create heat, damage the organism, or may otherwise be "wasted." In some cases, high intensity light may damage a cell in a way that results in decreased photosynthetic efficiency, decreased growth rate, or even death of the cell.

FIG. 1 illustrates an exemplary saturation response of a photosynthetic cell, according to some embodiments. FIG. 1 illustrates a schematic response 100 describing photosynthetic rate 110 as a function of light intensity 120. Photosynthetic rate 110 may represent or be represented by photosynthetic productivity, photosynthetic efficiency, electron transport rates, lipid productivity, biomass productivity, oxygen production, CO2 sequestration, and the like. Photosynthetic rate 110 may be associated with Photosystem I and/or II production. In some cases, photosynthetic rate 110 may represent an electron transport rate associated with PSII.

Response 100 may include a substantially "linear" regime 130 and a saturation regime 140. Linear regime 130 and saturation regime 140 may be separated by a threshold 150. Threshold 150 may be broad or narrow, and may be empirically associated with a transition between regimes. Threshold 150 may vary among diverse photosynthetic organisms—trees, grasses, corn, sugarcane, algae, diatoms, rhizomes such as switchgrass (*Panicum*), prairie grass (e.g., *Miscanthus*), and the like. For some algae (e.g., *Nannochloropsis*), a threshold 150 may be near 200 μmol quanta/m^2-sec. In some cases, a relatively "maximum" photosynthetic rate Pmax 152 may be defined. Threshold 150 may be associated with a light intensity such as Ek 154, which may represent an irradiance level at which an optimum photosynthetic rate is achieved.

Linear regime 130 may be associated with a region of light intensity in which photosynthetic rate 110 is approximately linearly dependent upon light intensity 120. A linear regime 130 may be characterized as a "light limited" regime, in that photosynthetic productivity is ostensibly limited by the available light, not by the cell per se. In some cases, an organism may be characterized by a slope 132 associated with linear regime 130. For some organisms, slope 132 of the photosynthetic rate vs. intensity response may be associated with a quantum yield of Photosystem II photochemistry. Slope 132 may be characterized by one or more metrics, (e.g., moles of O2 evolved per number of incident photons, mass of CO2 converted to biomass per input energy, and the like).

Saturation regime 140 may be characterized by a photosynthetic rate below what would be expected based on an extrapolation of the response in linear regime 130 (to higher intensities). For example, an observed photosynthetic rate 160 at intensity 162 may be below an extrapolated photosynthetic rate 164 (based on extrapolating from linear regime 130, e.g. using slope 132). An organism receiving an intensity in saturation regime 140 (e.g., at intensity 162) may use a relatively smaller percentage of the incident light for photosynthesis, as compared to an organism in linear regime 130. Such an exposure may overwhelm the photosynthetic capabilities of the organism, resulting in a relatively larger amount of the light not being utilized for photosynthesis. Such an exposure may be characterized by a lost productivity 170, which may be associated with a difference between actual photosynthetic rate and a photosynthetic rate that might be expected based on a productivity response at lower intensities (e.g., in a light limited regime).

Photosynthetic cells may be exposed to a wide range of light intensities. In some cases, a single organism may have some cells that are exposed to bright light, while other cells are exposed to weaker light. In some cases, single cells or single celled organisms (e.g., algae, diatoms, and the like) may be exposed to a range of light intensities. For example, algae in water may circulate from the surface (where light is intense) to a depth beneath the surface at which light is faint. Certain embodiments include maximizing a number of organisms exposed to an intensity near (or below) threshold 150.

Figure 2A:
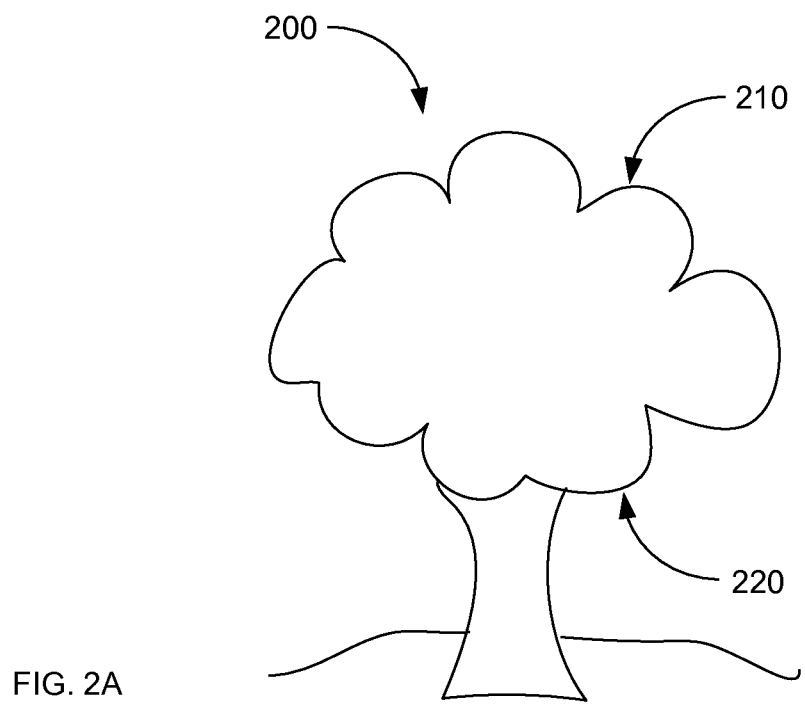
FIGS. 2A and 2B illustrate variations in light intensity for exemplary pluralities of photosynthetic cells.
Figure 2B:
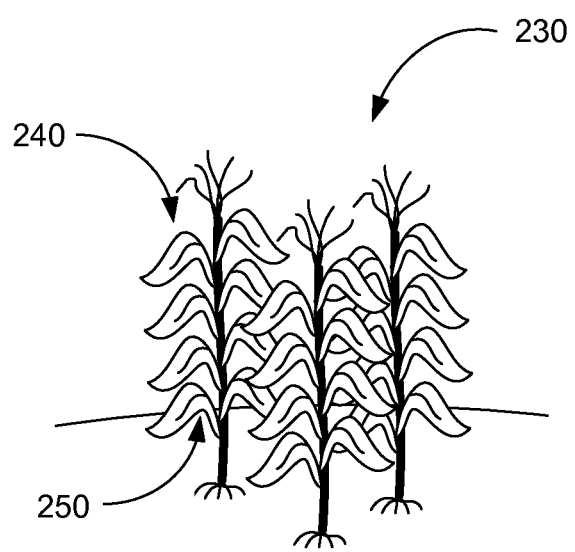

FIGS. 2A and 2B illustrate variations in light intensity for exemplary pluralities of photosynthetic cells. FIG. 2A illustrates a tree 200 having some cells 210 exposed to bright light, and other cells 220 exposed to weaker light. In some cases, cells 210 may at least partially shade cells 220. Exemplary organisms include firs, pines, poplars, and other plants.

FIG. 2B illustrates a plurality of photosynthetic organisms having cells exposed to a different light intensities. Crop 230 may include one or more plants for which some cells 240 are exposed to more intense light, and other cells 250 are exposed to less intense light. Exemplary crops 230 include corn, oats, wheat, barley, rice, sugarcane, beets, bamboo, palm, jatropha, various grasses such as prairie grasses, halophytes (e.g., *Spartina, Salicornia*, and the like) and/or other plants.

Figure 3A:
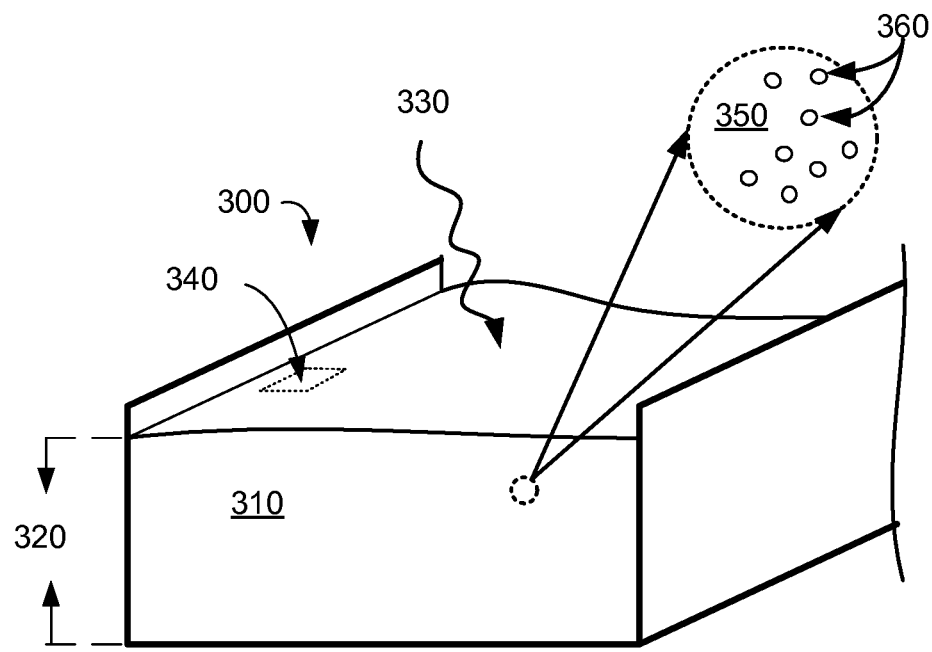
FIG. 3A illustrates an exemplary suspension.

FIG. 3A illustrates an exemplary suspension. In this example, an exemplary pond 300 has sides and a bottom, and is sufficiently deep to contain a suspension 310 at a depth 320. Suspension 310 may be characterized by a surface that "faces" a source of light. In FIG. 3A, a top surface of the suspension 310 faces light 330 (e.g., sunlight) arriving in an incident direction. The facing surface (e.g., the top surface) of suspension 310 may be characterized by an area 340. Suspension 310 may include a liquid 350 and a suspended phase 360.

Liquid 350 may include aqueous media such as water, seawater, fresh water, brackish water, growth media, and the like. Suspended phase 360 may include suspended photosynthetic organisms, such as algae, diatoms, and the like. Exemplary algae may include members of the genus *Nannochloropsis*. Exemplary diatoms may include members of the genera *Navicula, Amphora, Thallasiosira, Chaetoceros, Nitzschia, Cyclotella, Skeletonema, Phaeodactylum, Achnanthes, Coscinodiscus, Cylindrotheca, Pseudo-Nitzschia, Thalassionema, Hantzschia, Cymbella*, and/or *Psammodictyon*. Liquid 350 may include an aqueous liquid, such as water, seawater, synthetic seawater, brackish water, growth media, and the like.

Figure 3B:
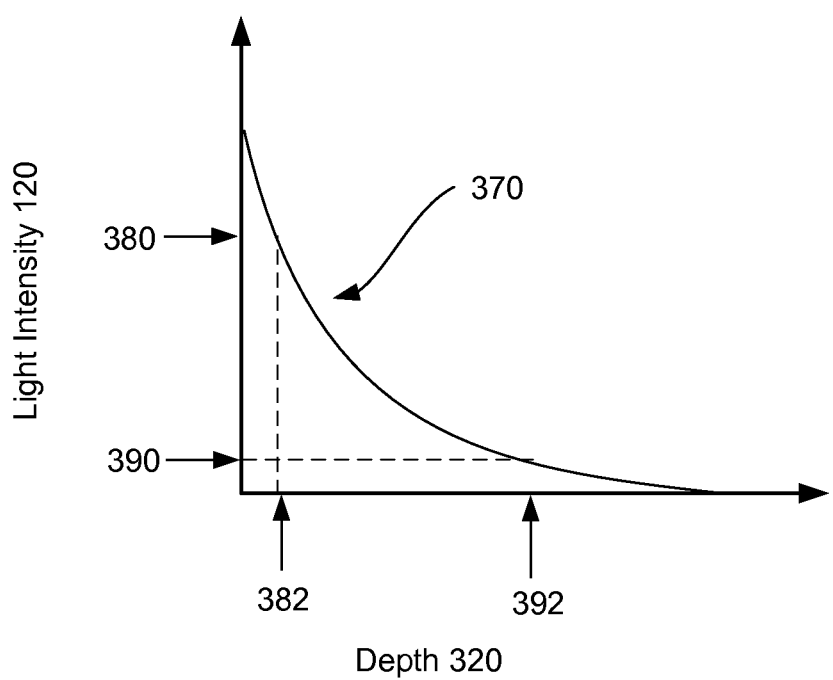
FIG. 3B is a schematic illustration of an exemplary variation in light intensity with depth through a plurality of cells (e.g., within a suspension).

FIG. 3B is a schematic illustration of an exemplary variation in light intensity with depth through a plurality of cells (e.g., within a suspension). FIG. 3B illustrates a relationship 370 between light intensity 120 and depth 320 under a set of conditions. For example, relationship 370 may represent a measured light intensity at various depths within suspension 310, at a particular incident light intensity, for a given concentration of certain organisms in a liquid having a certain composition. A first intensity 380 may be associated with a shallow depth 382 (e.g., at or near the top surface), and may be a relatively brighter light condition. A second intensity 390 may be a lower intensity of light at a deeper depth 392.

The light intensity within the suspension may scale with the incident light intensity. For example, first intensity 380 at mid-day on a sunny day in the tropics may correspond to an intensity in a saturation regime 140 (FIG. 1) (e.g., intensity 162, FIG. 1), and second intensity 390 and may correspond to an intensity corresponding to a "light limited" regime of some organisms, such as linear regime 130 (FIG. 1). On a less-bright day (e.g., a cloudy day), first intensity 380 may correspond to an intensity associated with threshold 150 (FIG. 1) or even a linear regime 130, and second intensity 390 may correspond to a light level below which photosynthesis may not occur. In some cases, second intensity 390 may correspond to a relatively dark "repair" intensity at which a photosynthetic cell may repair damage to itself. On a particular day and time, some cells may be "overexposed" to light, some cells may be "underexposed" to light, and some cells may receive an optimal amount of light (e.g., an intensity at or near threshold 150).

Many photosynthetic organisms adapt or acclimate to different light conditions. In some cases, a cell residing for significant time (e.g., hours or days) at a weak intensity may adapt to those weak light conditions, and may increase its sensitivity to light. A cell residing at a high intensity (e.g., intensity 380 on a sunny day) may adapt to bright light conditions, and may decrease its sensitivity to light. In some cases, sensitivity may be adjusted by adjusting one or more light harvesting antennae (LHA). Sensitivity may be adjusted by adjusting a violaxanthin-chlorophyll-a protein (VCP).

A cell that has adapted to weak-light conditions may have a "sensitized" LHA. Exposing such a "sensitized" cell to bright light may saturate or "overpower" the LHA, which may result in a substantial portion of the incident bright light not being used for photosynthesis. In some cases, bright light may result in an increased amount of non-photochemical quenching (NPQ), and/or an increased ratio of NPQ to photosynthetic absorption. In some cases, cells that are adapted to weak intensity may be damaged by a high intensity.

A cell that has acclimated to intense light may not harvest as much weak light as a cell that has acclimated to weak light. In some cases, a cell may "reduce the gain" of a light harvesting antenna in response to intense light, which may allow for a relatively larger fraction of light to pass through the cell without being absorbed by the antenna. In some cases, a reduction in LHA sensitivity may be manifest as a reduced slope 132 (FIG. 1) as compared to the slope characterizing a cell having a standard LHA (e.g., a wild type).

Cells nearer to an incident light source (e.g., at the top of a tree or top of a suspension) may absorb some incident light, and a portion of the incident light may pass through the cells to the "shaded" cells beneath or behind the nearer cells. Light that has passed through a first cell may be absorbed by a second cell. In some embodiments, an overall efficiency of a plurality of photosynthetic cells may be increased by reducing the amount of light absorbed each individual cell, and more particularly, by minimizing an amount of light that is absorbed via non-photosynthetic processes (e.g., NPQ). In some embodiments, a plurality of cells are engineered to have an increased transparency via a reduced LHA sensitivity. By minimizing the scattering and/or absorption of light via non-photosynthetic mechanisms (e.g., NPQ, dissipation of light as heat, ionization, damage, and the like), light that is not used for photosynthesis by a first cell may pass through the first cell be available for use by a second cell.

In some cases, a reduction in each individual cell's ability to harvest light may result in an increase in the overall efficiency of a population of the cells. A reduction in light harvesting efficiency results in greater transmittance of light through a cell, which increases the light available to other cells. A reduction in LHA efficiency may be manifest as an increased transparency of the cell (and/or a plurality of such cells).

Figure 4:
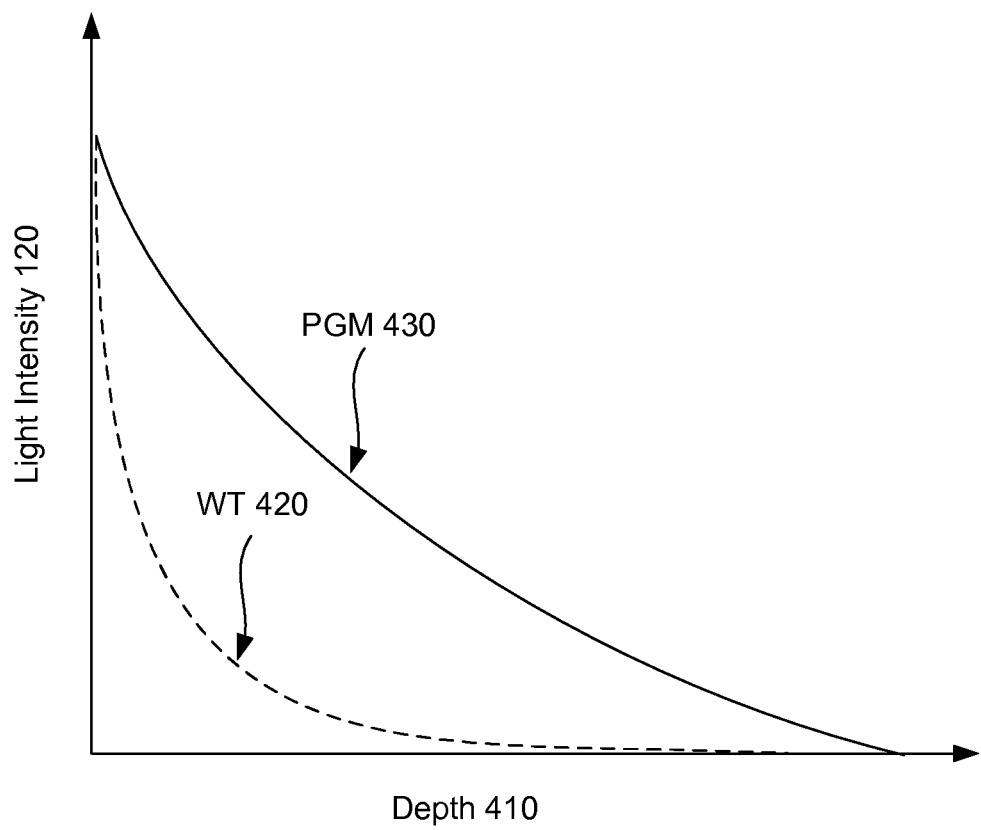
FIG. 4 is a schematic illustration of an effect of increased transparency, according to some embodiments.

FIG. 4 is a schematic illustration of an effect of increased transparency, according to some embodiments. FIG. 4 illustrates two variations in measured light intensity 120 as a function of depth 410 in two suspensions, and may be determined by measuring an intensity of light at various depths (or distances from the surface facing the light) of the suspension. A first organism WT 420 may be a native, wild type, or other unmodified organism. A second organism PGM 430 may include a modified transparency, and in some cases, may be characterized by an increased transparency as compared to WT 420. A suspension of PGM 430 cells may attenuate light less than a corresponding suspension of WT 420 cells, as illustrated in FIG. 4.

In some embodiments, transparency may be increased by reducing a size and/or number of LHA. In some cases, transparency may be increased by decreasing an amount of chlorophyll in the cell (e.g., an amount of chlorophyll associated with one or more LHA). In some cases, a transparency may be increased by decreasing an amount of chlorophyll in apparatus associated with Photosystem I. In some cases, a transparency may be increased by decreasing an amount of chlorophyll in apparatus associated with Photosystem II (PSII). In some cases a transparency may be increased by decreasing an amount of carotenoid (e.g., Violaxanthin) with and/or within a LHA.

Figure 5:
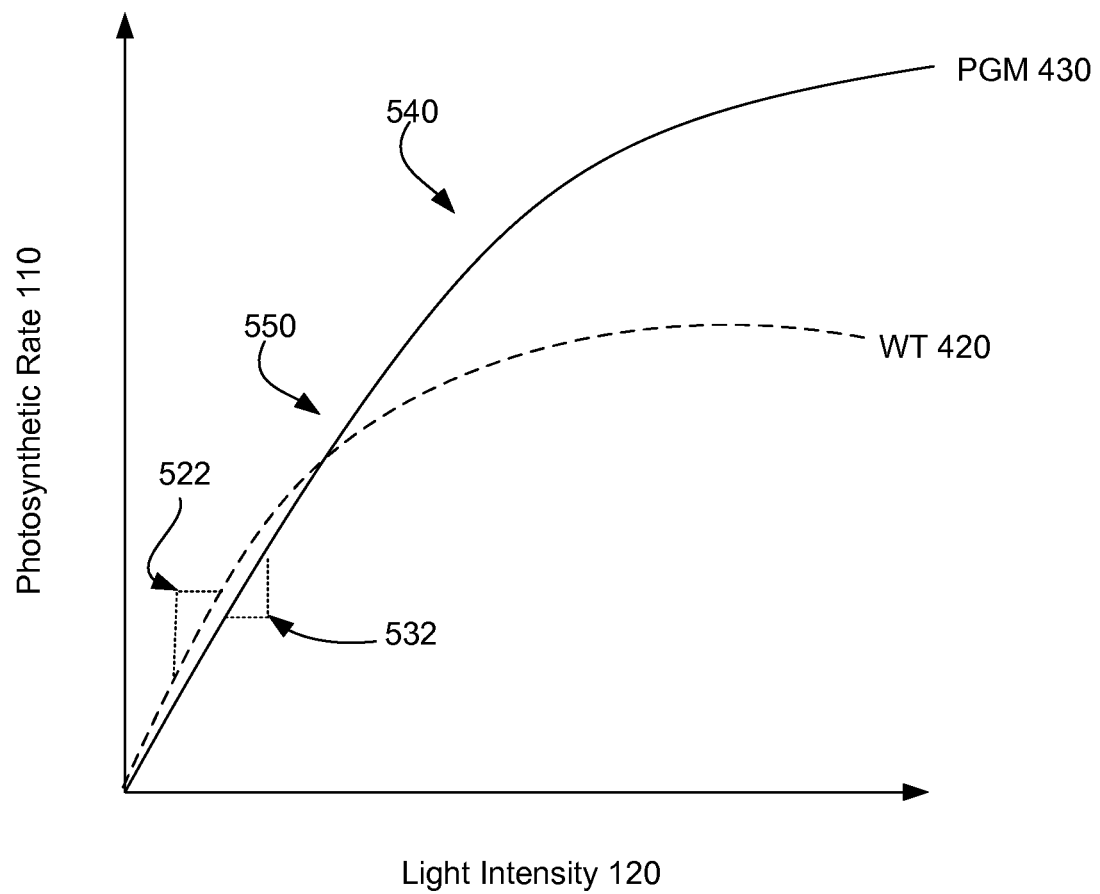
FIG. 5 illustrates a schematic comparison of two photosynthetic rate responses, according to some embodiments.

FIG. 5 illustrates a schematic comparison of two photosynthetic rate responses, according to some embodiments. FIG. 5 is a schematic graph of photosynthetic rate 110 as a function of incident light intensity 120. In some embodiments, Photosynthetic rate 110 is associated with a Photosystem II electron transport rate. FIG. 5 compares responses for two organisms, a wild type organism WT 420 and a modified organism PGM 430. In some embodiments, PGM 430 may reach a higher photosynthetic rate 110 than WT 420, at one or more light intensities. In some cases, PGM 430 has a higher maximum photosynthetic rate than does WT 420. PGM 430 may have a linear regime characterized by a slope 532 that is lower than the corresponding slope 522 of WT 420. In some cases, PGM 430 may have a threshold 550 that is higher than the corresponding threshold 560 of WT 420. PGM 430 may have a higher slope at high light intensities (e.g., above threshold 540) than does WT 420. At some particularly high light intensities, the photosynthetic rate of WT 420 may decrease with increasing intensity, whereas the photosynthetic rate of PGM 430 at those intensities may not decrease as much or at all.

Figure 6:
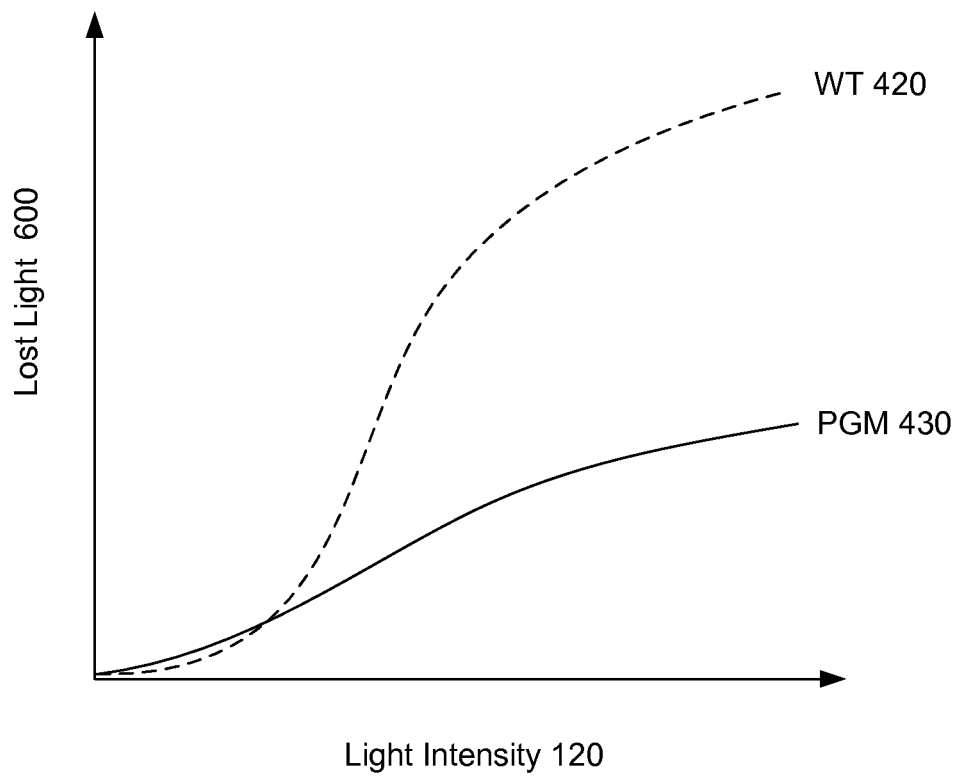
FIG. 6 illustrates a schematic comparison of light loss as a function of light intensity, according to some embodiments.

FIG. 6 illustrates a schematic comparison of light loss as a function of light intensity, according to some embodiments. Light loss 600 may characterize an amount of light incident on a cell that is not used for photosynthesis. Light loss 600 may be associated with various dissipation mechanisms, such as NPQ, a conversion of light to heat, photoinduced ionization, and the like. In some embodiments, an unmodified organism WT 420 may lose or otherwise dissipate more light than a modified organism PGM 430, particularly at high light intensities.

Figure 7:
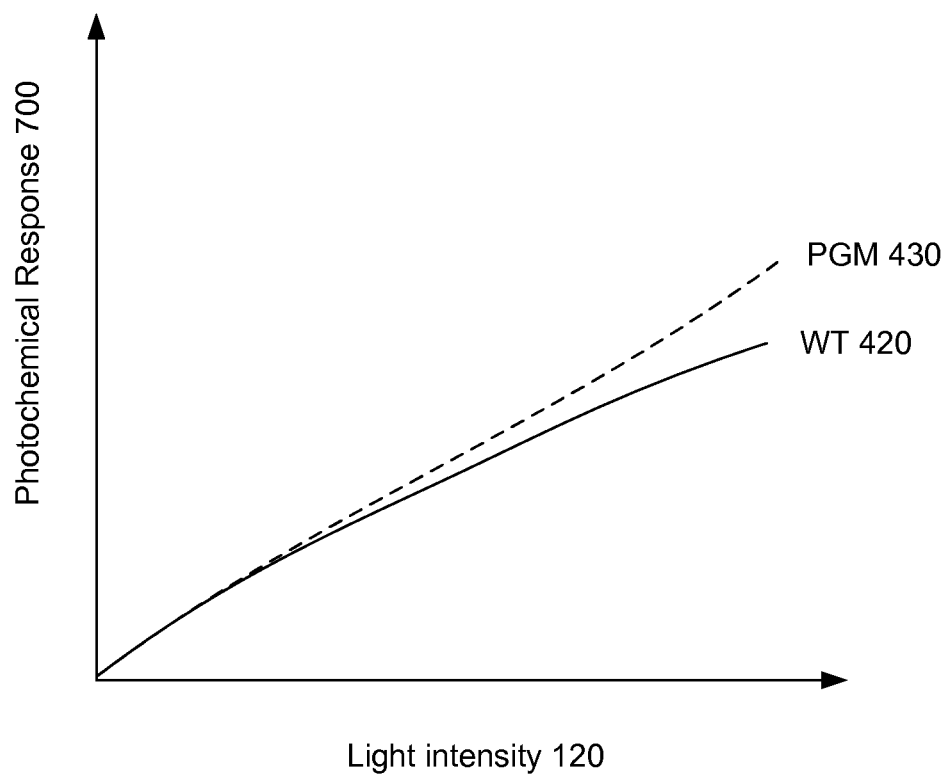
FIG. 7 illustrates a schematic comparison of photochemical responses, according to some embodiments.

FIG. 7 illustrates a schematic comparison of photochemical responses, according to some embodiments. Photochemical response 700 may include a response such as a Photosystem I electron transport rate. In some embodiments, WT 420 and PGM 430 may have similar photochemical responses 700. In some cases, a WT 420 and a PGM 430 may display similar first photochemical responses (e.g., PS I electron transport rate) while having different second photochemical responses (e.g., PS II electron transport rate).

In some embodiments, PGM 430 may display a different photochemical response 700 as compared to WT 420 (e.g., higher slope and/or higher maximum). In some cases, this difference may increase with time (e.g., exposure time, growth time, replications, and the like). This difference may vary with irradiant intensity.

Figure 8:
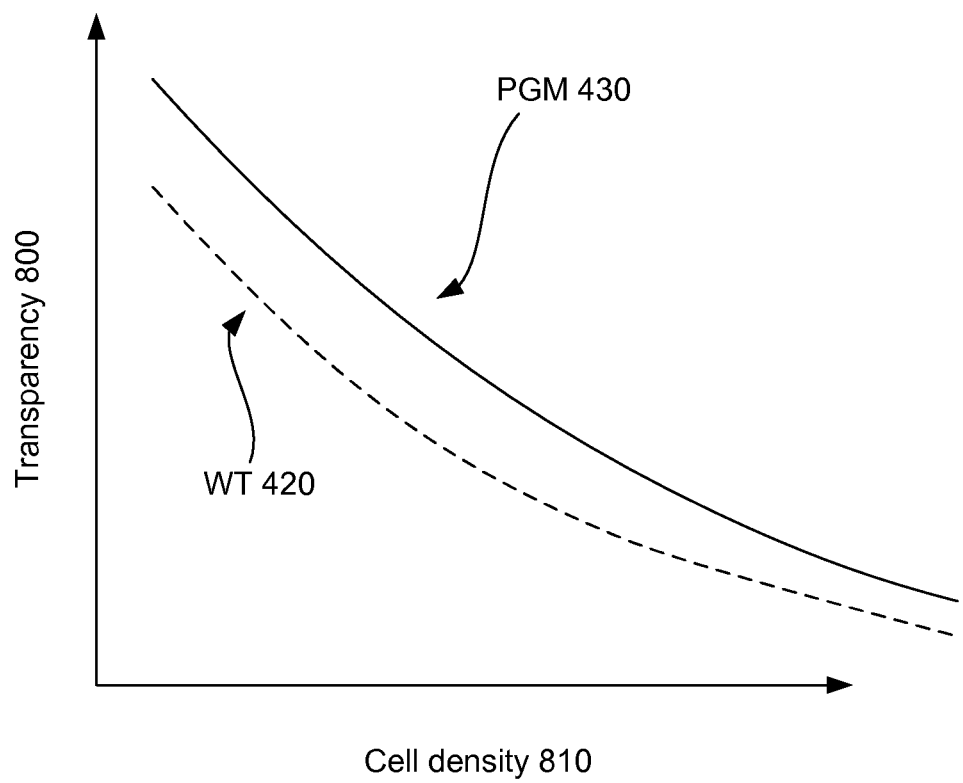
FIG. 8 illustrates a schematic comparison of transparency as a function of cell density, according to some embodiments.

FIG. 8 illustrates a schematic comparison of transparency as a function of cell density, according to some embodiments. Transparency 800 may be measured as a function of incident light intensity, depth, cell density (e.g., number of cells per volume of liquid), and the like. Transparency may be measured using an apparatus having a defined path length and light intensity. Transparency may be measured by measuring light intensity at one or more points within a suspension as a function of incident intensity. Cell density measurements (e.g., cell counting over a volume) may be used to differentiate among factors affecting transparency (e.g., cell transparency vs. number of cells). In some cases, cell density 810 may include a response associated with cell replication (e.g., new cells growing) and/or adapting to light conditions (e.g., cell density). In some cases, cell density 810 may include a response associated with cells adapting to light (e.g., high cell densities and corresponding decreased mean intensities may result in adaptation of LHA apparatus).

At one or more cell densities 810, modified organism PGM 430 may have an increased transparency as compared to unmodified organism WT 420. Increased transparency may be manifest as an increased measured light intensity at a point within a suspension of modified organisms, as compared to an equivalent measurement (e.g., at equal cell density) within a suspension of unmodified organisms.

Figure 9:
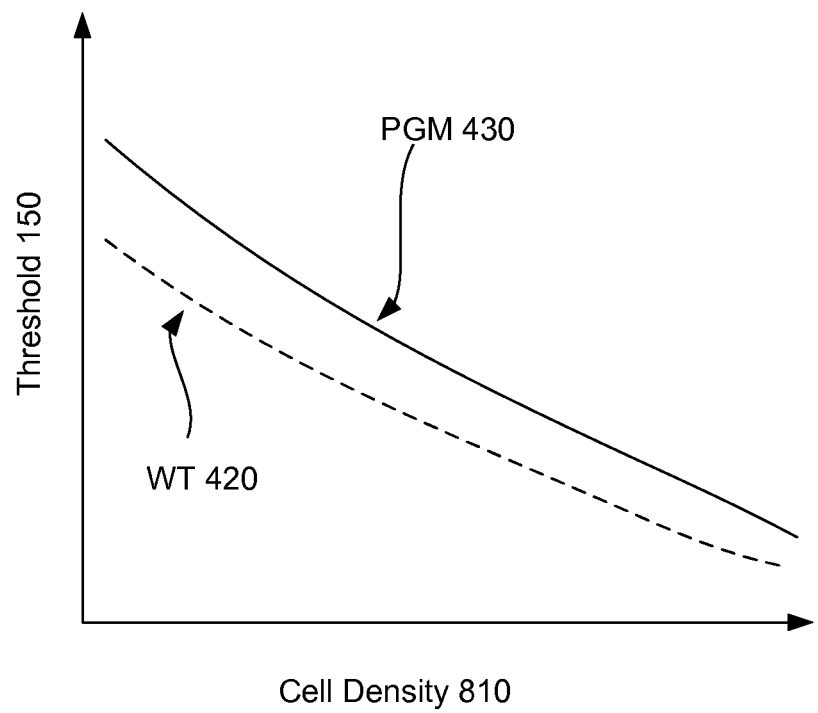
FIG. 9 illustrates a schematic comparison of the transition thresholds of modified and unmodified cells, according to some embodiments.

FIG. 9 illustrates a schematic comparison of transition thresholds of modified and unmodified cells, according to some embodiments. FIG. 9 schematically compares a response of a modified organism PGM 430 to that of an unmodified organism WT 420. An exemplary transition is shown as threshold 150 in FIG. 9, although other transitions (e.g., Ek) may be used. In some cases, a transition may characterize an irradiance level for optimal photosynthetic productivity. In some cases, increasing cell density may be associated with growth of cells.

Figure 10:
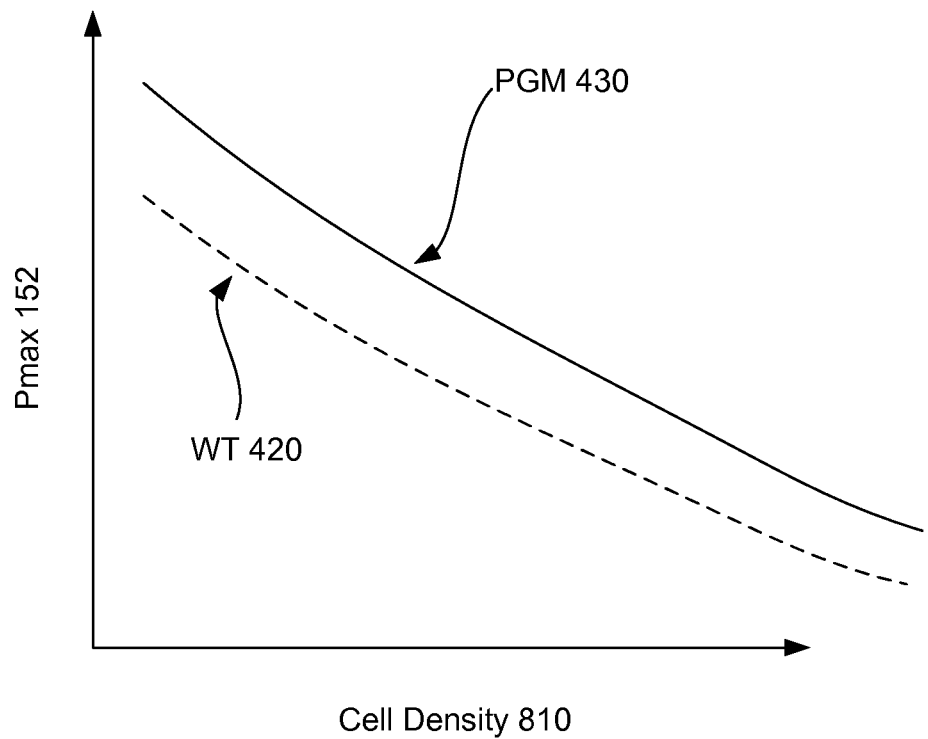
FIG. 10 illustrates a schematic comparison of maximum photosynthetic rates, according to certain embodiments.

FIG. 10 illustrates a schematic comparison of maximum photosynthetic rates, according to certain embodiments. FIG. 10 schematically compares a response of a modified organism PGM 430 to that of an unmodified organism WT 420. In this example, extracted values of Pmax 152 are shown as a function of cell density 810.

Figure 11:
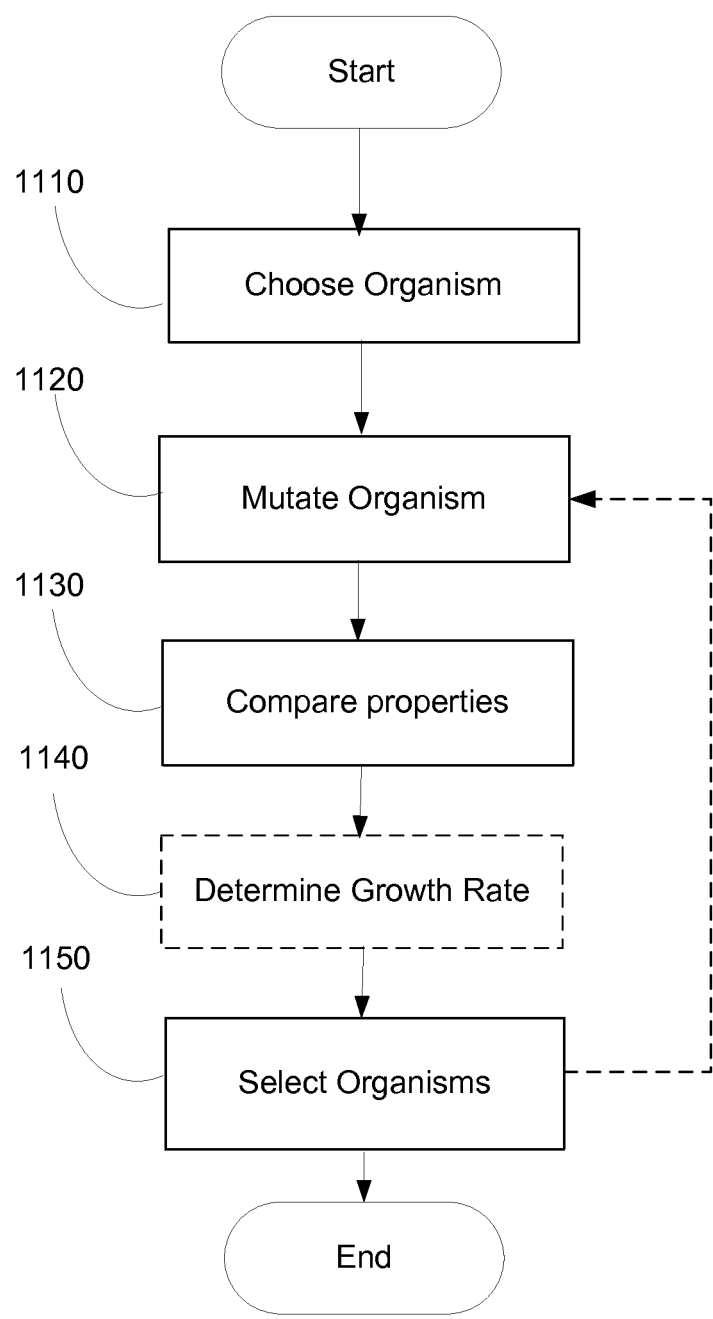
FIG. 11 illustrates an exemplary method.

FIG. 11 illustrates an exemplary method. A starting (e.g., native or wild type) organism is chosen in step 1110. In step 1120, the organism is mutated (e.g., using mutagenesis) to create one or more mutated organisms. One or more properties of the organisms may be compared in step 1130, which may include selecting one or more mutated organisms. Selecting may include using fluorescence activated cell sorting to select cells based on certain optical properties. Certain embodiments include screening based on phenotypes. In some cases, a specific genetic sequence may be modified (e.g., a genetic sequence that reduces an efficacy of a light harvesting antenna may be incorporated into an organism).

Properties to be screened for and compared may include transparency, threshold, Pmax, PSII properties, PSI properties, NPQ, and the like. In some cases, properties may include optical properties, and may include properties that may be rapidly screened for and/or measured. In some cases, organisms may be selected using quickly screenable properties (e.g., transparency). A selected subset may be further screened for properties that may take longer to evaluate (e.g., growth rates).

In optional step 1140, growth rates may be compared. One or more mutated organisms may be selected in step 1150. In some cases, a selected organism may have a higher growth rate than the wild type equivalent, and may also have certain properties (e.g., as determined in step 1130) that distinguish it from the wild type organism. A selected mutated organism may have an increased transparency, a higher PSII ETR, a lower NPQ, a paler color, a different fluorescence spectrum and/or intensity, and the like.

In some embodiments, cells may be subjected to mutagenesis, and the mutated cells may be grown. Mutated cells having increased transparency as compared to native cells may be selected. In some cases, cells having increased transparency may be further selected based on growth rates (e.g., choosing those cultures with the highest growth rates). In certain cases, cultures having high growth rates under high light conditions and high cellular densities are selected.

EXAMPLE 1

Random Mutagenesis Using ICR-191

*Nannochloropsis* sp. (e.g., *Oceanica*) were mutated and their properties measured. ICR-191 was prepared as a stock solution at a concentration of 1 mg/ml in 0.1N filter sterilized HCl. Cells were grown to mid-log phase and diluted to $10^6$ cells/ml. To 20 ml of the diluted culture 40 μl of the ICR-191 stock was added. Flasks were placed on a shaker and illuminated at 50 μmol quanta $m^{-2}s^{-1}$. Following 7 days of growth cells were washed twice with growth medium and then plated on agar plates. After 3-4 weeks of growth on plates relatively pale green colonies were selected, re-suspended in medium and then re-plated on fresh agar plates.

Fluorescence and Spectroscopic Analysis of Photosynthetic Function

Pulse amplitude modulated (PAM) fluorescence was recorded at the growth temperature of the culture using a Dual-PAM (Walz, Effeltrich, Germany). Samples were illuminated with visible light using the red LED built into the Dual-PAM. Samples were dark adapted in the sample chamber for a minimum of 10 min prior to all measurements. The actual photochemical efficiency of PSII at any given actinic irradiance was calculated as Fm'-Fs/Fm'. The relative PSII ETR was calculated as the product of the actual photochemical efficiency of PSII and the actinic irradiance. NPQ was measured as Fm-Fm'/Fm'. In addition to PSII ETR, simultaneous measurements of PSI ETR were made. The photochemical efficiency of PSI at any given actinic irradiance was calculated as 1-(Y(ND)+Y(NA)). PSI ETR was then calculated as the product of Y(I) and the actinic irradiance.

Figure 12A:
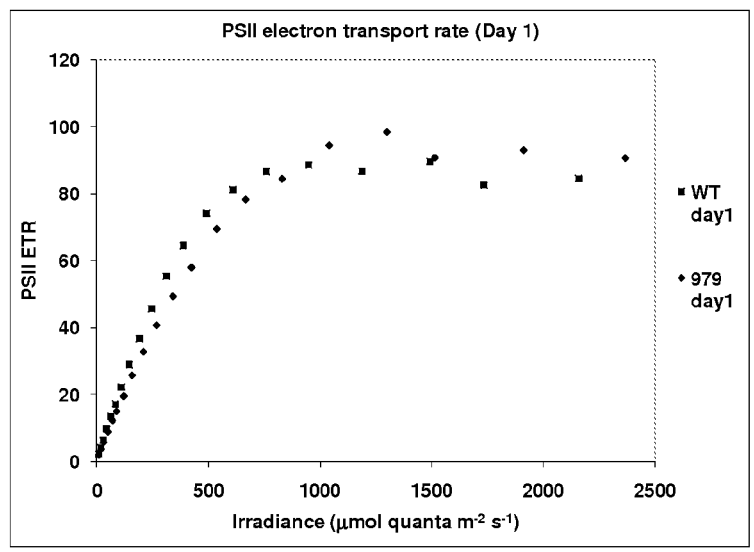
FIGS. 12A, 12B, and 12C illustrate experimental results for wild type (annotated WT) and mutated (annotated 979) samples after day 1 of growth.
Figure 12B:
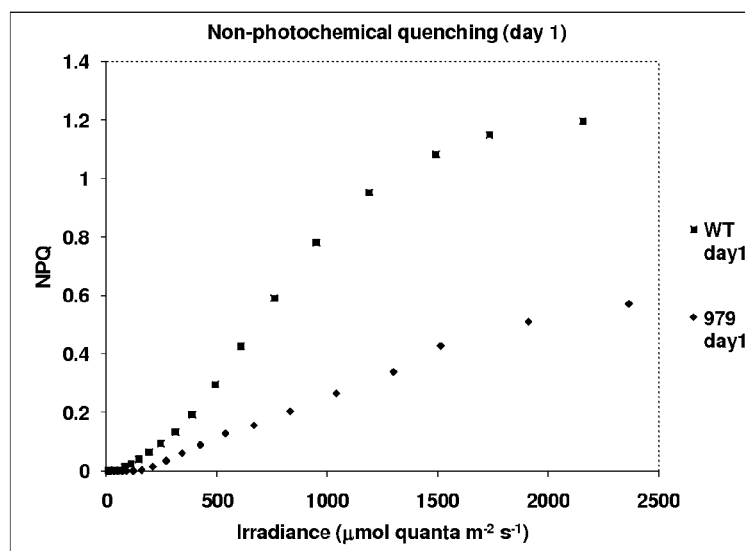
Figure 12C:
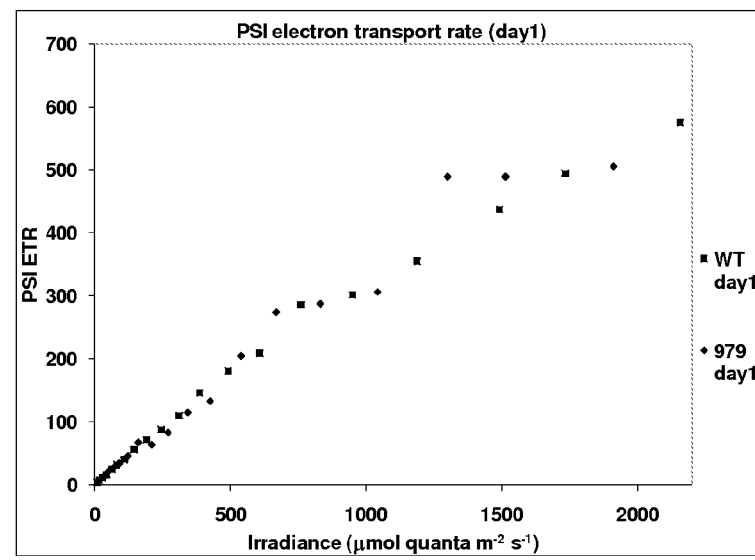

FIGS. 12A, 12B, and 12C illustrate experimental results for wild type (annotated WT) and mutated (annotated 979) samples after day 1 of growth. FIG. 12A illustrates PSII electron transport rate (ETR) data as a function of irradiance. FIG. 12B illustrates NPQ as a function of irradiance. FIG. 12C illustrates PSI ETR as a function of irradiance.

Figure 13A:
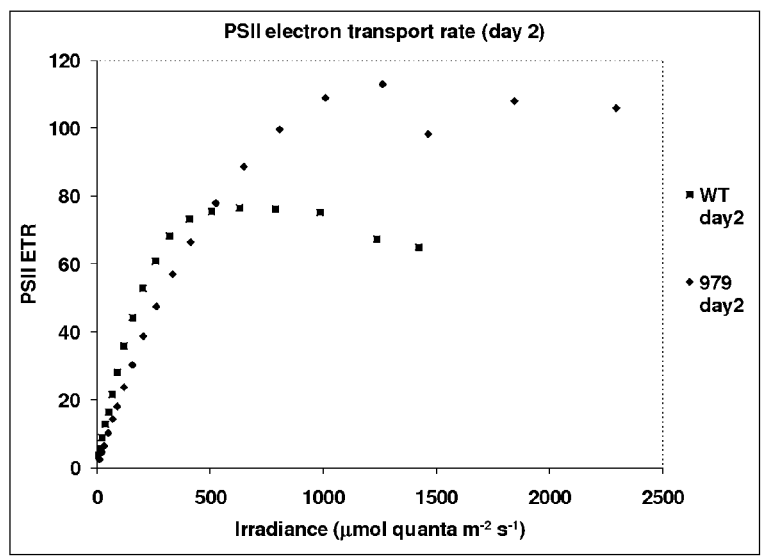
FIGS. 13A, 13B, and 13C illustrate experimental results for wild type (annotated WT) and mutated (annotated 979) samples after day 2 of growth.
Figure 13B:
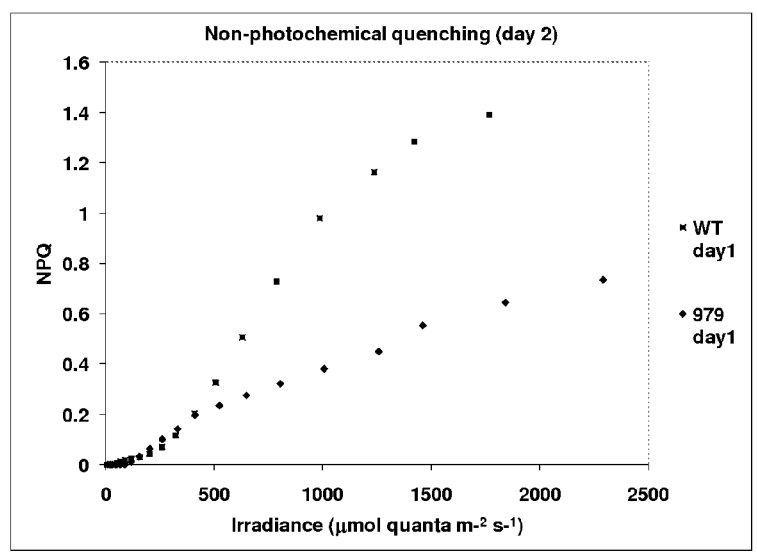
Figure 13C:
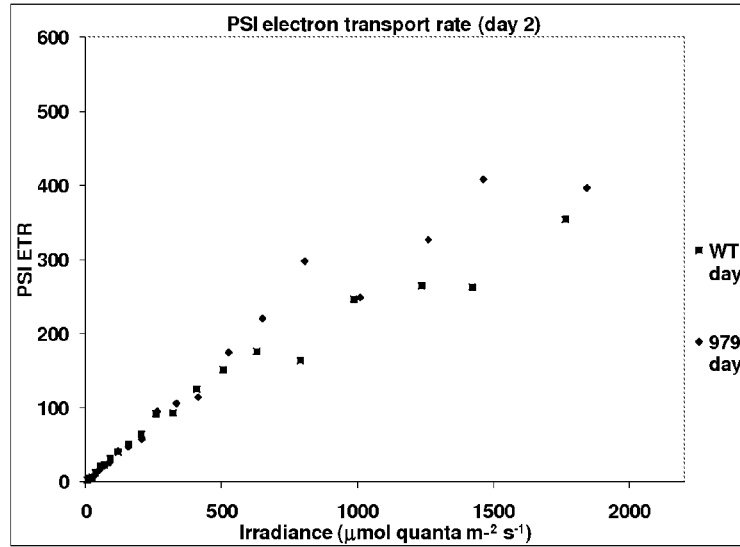

FIGS. 13A, 13B, and 13C illustrate experimental results for wild type (annotated WT) and mutated (annotated 979) samples after day 2 of growth. FIG. 13A illustrates PSII electron transport rate (ETR) data as a function of irradiance. FIG. 13B illustrates NPQ as a function of irradiance. FIG. 13C illustrates PSI ETR as a function of irradiance.

Figure 14A:
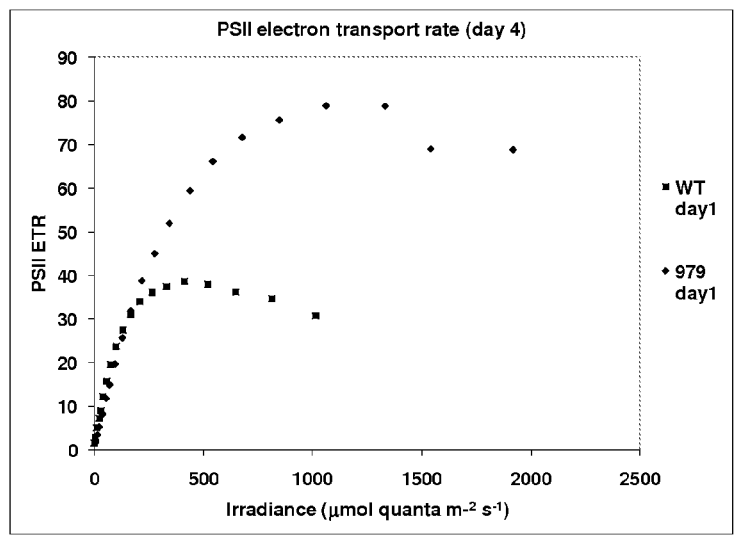
FIGS. 14A, 14B, and 14C illustrate experimental results for wild type (annotated WT) and mutated (annotated 979) samples after day 4 of growth.
Figure 14B:
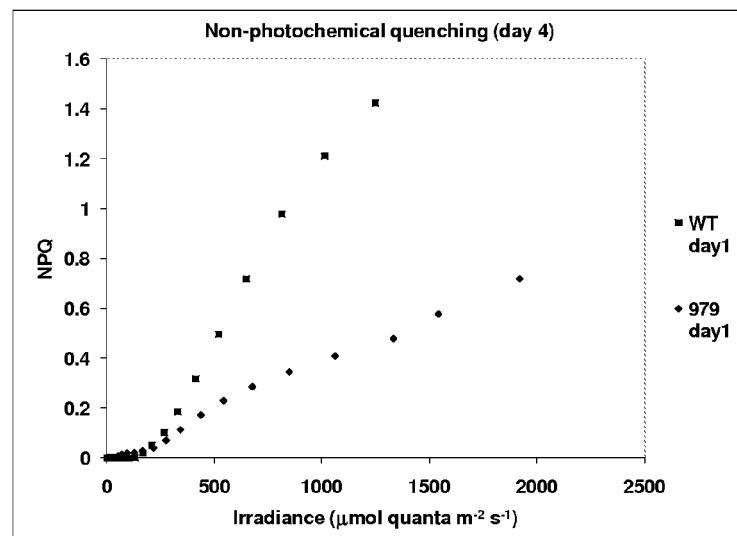
Figure 14C:
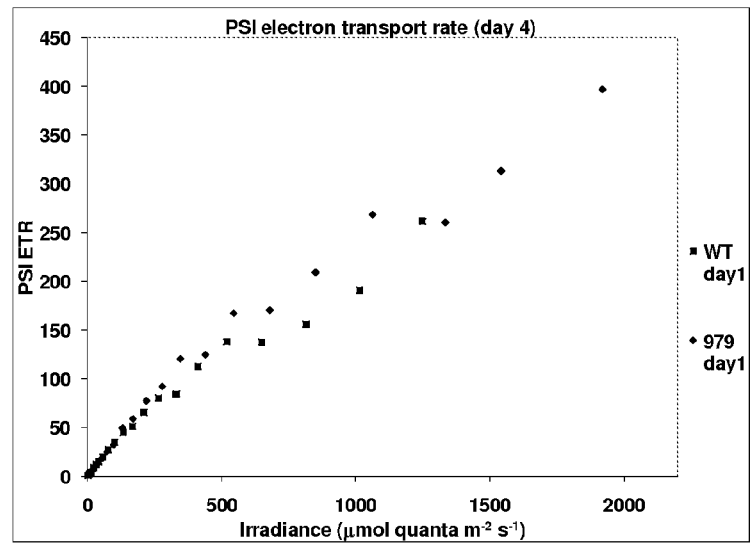

FIGS. 14A, 14B, and 14C illustrate experimental results for wild type (annotated WT) and mutated (annotated 979) samples after day 4 of growth. FIG. 14A illustrates PSII electron transport rate (ETR) data as a function of irradiance. FIG. 14B illustrates NPQ as a function of irradiance. FIG. 14C illustrates PSI ETR as a function of irradiance.

Figure 15A:
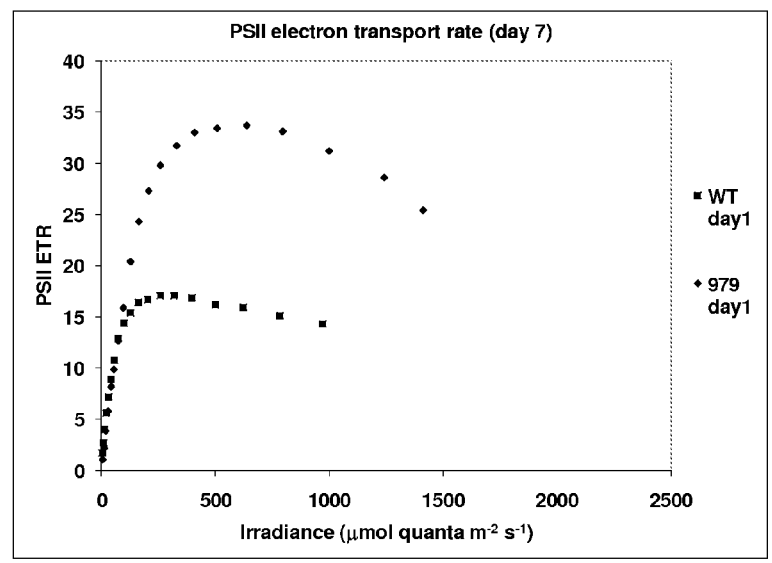
FIGS. 15A, 15B, and 15C illustrate experimental results for wild type (annotated WT) and mutated (annotated 979) samples after day 7 of growth.
Figure 15B:
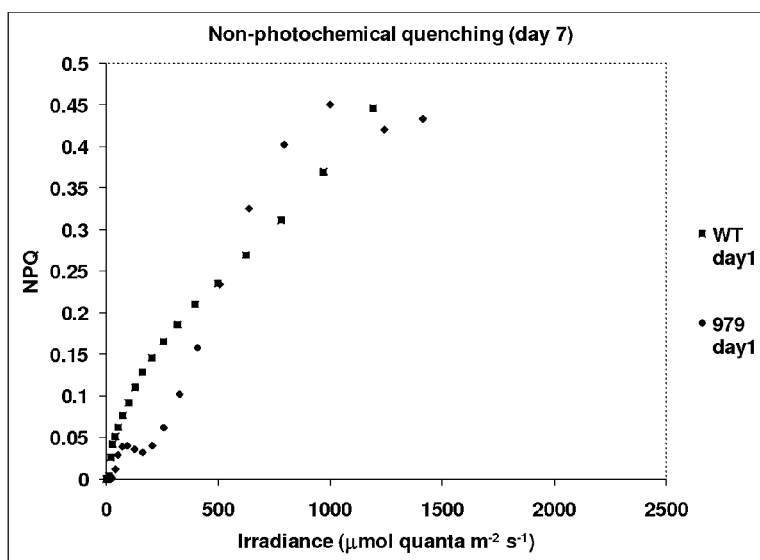
Figure 15C:
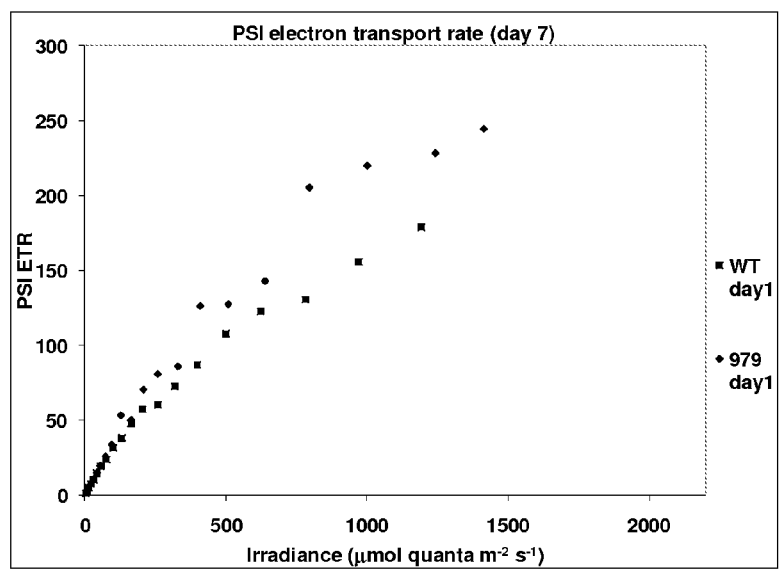

FIGS. 15A, 15B, and 15C illustrate experimental results for wild type (annotated WT) and mutated (annotated 979) samples after day 7 of growth. FIG. 15A illustrates PSII electron transport rate (ETR) data as a function of irradiance. FIG. 15B illustrates NPQ as a function of irradiance. FIG. 15C illustrates PSI ETR as a function of irradiance.

Figure 16:
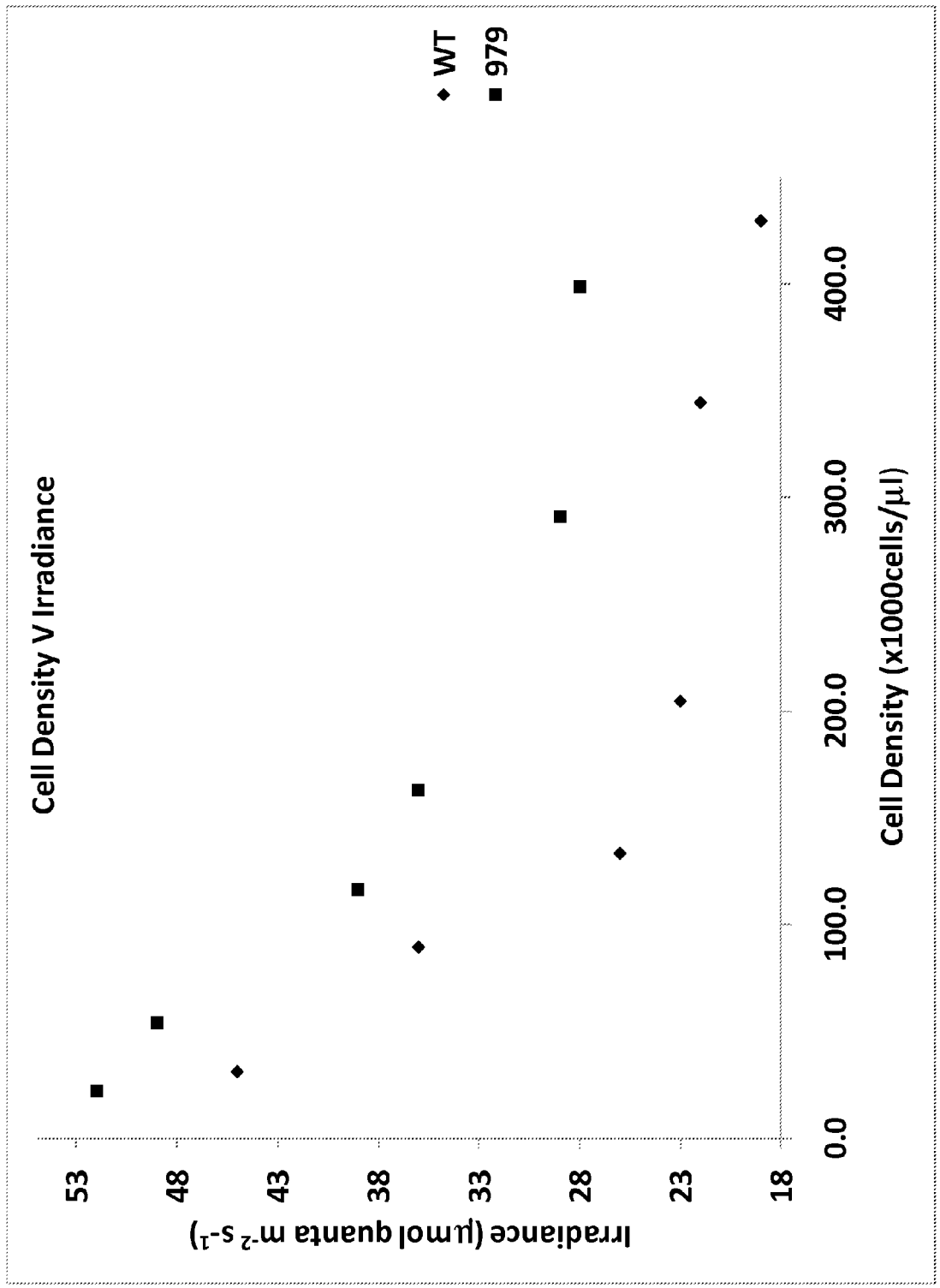
FIG. 16 illustrates a comparison of irradiance vs. cell density for wild type (annotated WT) and mutated (annotated 979) samples.

FIG. 16 illustrates a comparison of irradiance vs. cell density for wild type (annotated WT) and mutated (annotated 979) samples. In this example, "irradiance" generally describes a measured light intensity at a point within the suspension for a given incident intensity. Samples were measured at different lengths of growth time, generally corresponding to the days shown in FIGS. 12-15. Mutated sample 979 generally resulted in a more intense measured light intensity (higher irradiance) at a given cell density, as compared to the wild type sample WT.

Figure 17:
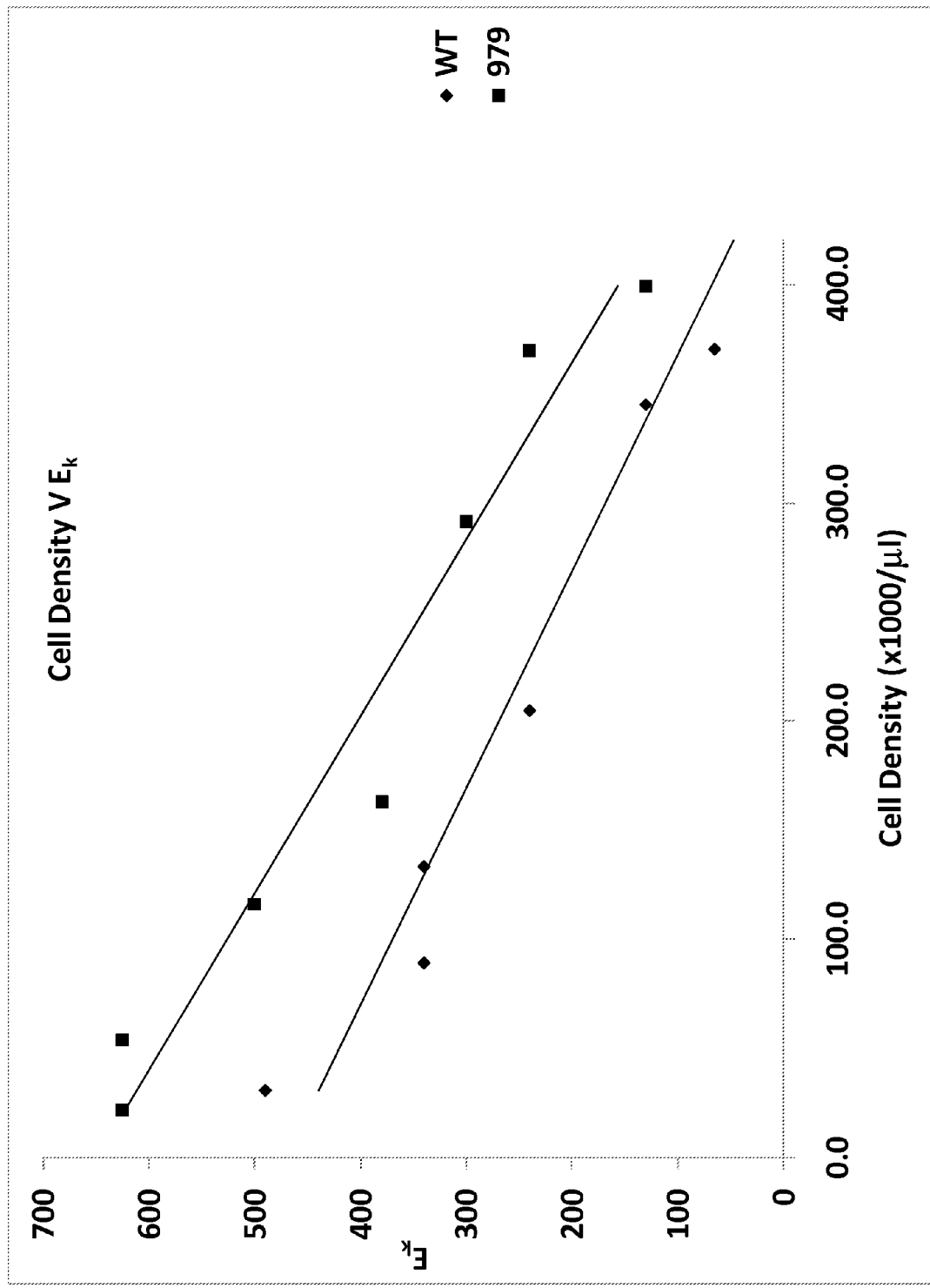
FIG. 17 illustrates a comparison of measured Ek vs. cell density for wild type (annotated WT) and mutated (annotated 979) samples.

FIG. 17 illustrates a comparison of measured Ek vs. cell density for wild type (annotated WT) and mutated (annotated 979) samples. In this example, Ek was estimated using the PSII ETR results of FIGS. 12-15. Mutated sample 979 generally displayed a higher Ek at a given cell density.

Figure 18:
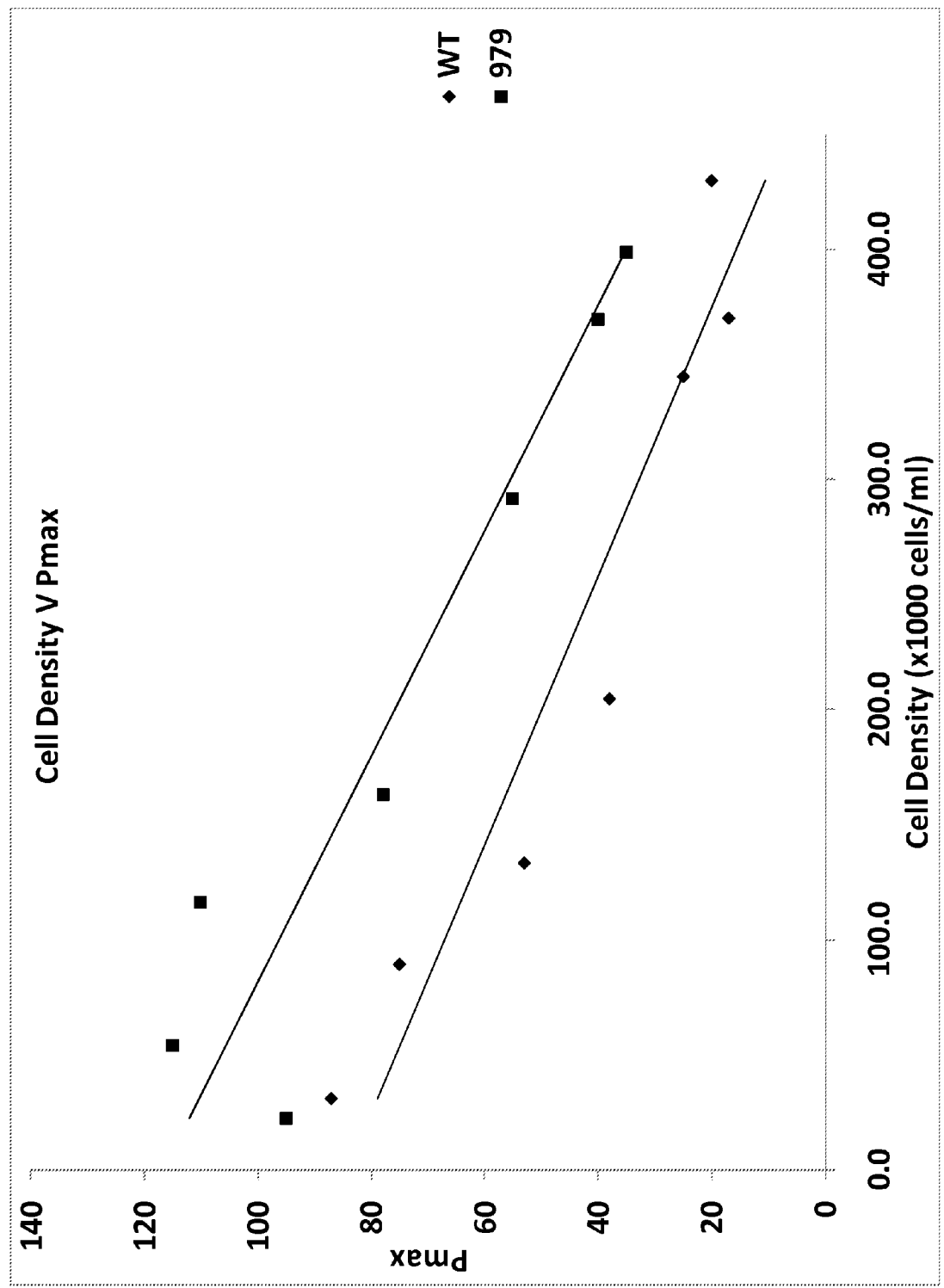
FIG. 18 illustrates a comparison of measured Pmax vs. cell density for wild type (annotated WT) and mutated (annotated 979) samples.

FIG. 18 illustrates a comparison of measured Pmax vs. cell density for wild type (annotated WT) and mutated (annotated 979) samples. In this example, Pmax is the maximum observed photosynthetic rate, and was estimated using the PSII ETR results of FIGS. 12-15. Mutated sample 979 generally displayed a higher Pmax at a given cell density.

Some embodiments include sensors to sense various parameters (e.g., light intensity, concentration, depth, photosynthetic rate, clarity, pH, mass, dielectric constant, transparency, opacity, time, date, and other characteristics). Apparatus may monitor various sensors, and systems may be actuated by automated controls (solenoid, pneumatic, piezoelectric, and the like). Some embodiments include a computer readable storage medium coupled to a processor and memory. Executable instructions stored on the computer readable storage medium may be executed by the processor to perform various methods described herein. Sensors and actuators may be coupled to the processor, providing input and receiving instructions associated with various methods. Certain instructions provide for closed-loop control of various parameters via coupled sensors providing input and coupled actuators receiving instructions to adjust parameters. Certain embodiments include materials. A biofuel may be synthesized from a carbohydrate, a lipid, and/or other biomass, which may be derived from cells and methods according to various embodiments.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A method for increasing cell density of photosynthetic organisms, the method comprising:
choosing a first photosynthetic organism having a first transparency and a first cell density associated with light transmission through the first photosynthetic organism;
subjecting the first photosynthetic organism to mutagenesis to create one or more second photosynthetic organisms;
determining a second transparency associated with light transmission through at least one of the second photosynthetic organisms; and
selecting one or more second photosynthetic organisms for which the second transparency is greater than the first transparency; the first photosynthetic organism being a member of genus Nannochloropsis and the selected one or more second photosynthetic organisms having a second cell density greater than the first cell density by at least 5%.

2. The method of claim 1, further comprising:
determining a first growth rate of the first photosynthetic organism;
determining a second growth rate of at least one of the second photosynthetic organisms; and
selecting one or more second photosynthetic organisms having the second growth rate larger than the first growth rate.

3. The method of claim 2, wherein at least one of the second photosynthetic organisms has the second growth rate larger than the first growth rate and has the second transparency greater than the first transparency.

4. The method of claim 2, wherein one or more growth rates include a measurement of total biomass.

5. The method of claim 2, wherein one or more growth rates include a measurement of lipid production.

6. The method of claim 1, wherein the first transparency and the second transparency are determined in the visible light regime.

7. The method of claim 1, wherein a color of the first photosynthetic organism is a first green, and at least one of the selected second photosynthetic organisms is a paler green than the first green.

8. The method of claim 1, wherein at least one of the selected second photosynthetic organisms has a less effective light harvesting antenna than does the first photosynthetic organism.

9. The method of claim 1, wherein at least one of the second photosynthetic organisms has a higher PSII electron transport rate than the first photosynthetic organism at a first irradiance.

10. The method of claim 9, wherein the first irradiance is associated with a saturation regime of the first photosynthetic organism.

11. The method of claim 1, wherein at least one of the second photosynthetic organisms has a lower value associated with nonphotochemical quenching than does the first photosynthetic organism at a first irradiance.

12. The method of claim 1, wherein at least one of the second photosynthetic organisms has a higher threshold irradiance than does the first photosynthetic organism.

13. The method of claim 1, wherein at least one of the second photosynthetic organisms has a higher maximum photosynthetic rate than does the first photosynthetic organism.

* * * * *